(12) United States Patent
Ueda et al.

(10) Patent No.: US 7,169,104 B2
(45) Date of Patent: Jan. 30, 2007

(54) MAGNETIC ANCHOR REMOTE GUIDANCE SYSTEM

(75) Inventors: Hirohisa Ueda, Saitama (JP); Kunitoshi Ikeda, Tokyo (JP); Tadao Kakizoe, Tokyo (JP); Toshiaki Kobayashi, Tokyo (JP); Takuji Gotoda, Tokyo (JP); Katsunori Tamakawa, Miyagi (JP)

(73) Assignees: Pentax Corporation, Tokyo (JP); National Cancer Center, Tokyo (JP); Tamakawa Co., Ltd., Miyagi (JP)

( * ) Notice: Subject to any disclaimer, the term of this patent is extended or adjusted under 35 U.S.C. 154(b) by 421 days.

(21) Appl. No.: 10/659,323

(22) Filed: Sep. 11, 2003

(65) Prior Publication Data

US 2004/0050395 A1    Mar. 18, 2004

(30) Foreign Application Priority Data

Sep. 13, 2002   (JP)   ............... 2002-268239

(51) Int. Cl.
*A61B 1/00* (2006.01)

(52) U.S. Cl. .................. 600/104; 600/12; 600/118; 128/899

(58) Field of Classification Search ............ 128/899; 600/104, 118, 201
See application file for complete search history.

(56) References Cited

U.S. PATENT DOCUMENTS

| 3,358,676 | A | | 12/1967 | Frei et al. |
| 5,681,260 | A | * | 10/1997 | Ueda et al. ............... 600/114 |
| 5,904,147 | A | * | 5/1999 | Conlan et al. ............. 128/899 |
| 6,293,282 | B1 | * | 9/2001 | Lemelson .................. 128/899 |
| 6,296,604 | B1 | | 10/2001 | Garibaldi et al. |
| 6,902,528 | B1 | * | 6/2005 | Garibaldi et al. ........... 600/118 |
| 2002/0033746 | A1 | | 3/2002 | Kuwahara |

FOREIGN PATENT DOCUMENTS

| JP | 63-44930 | 11/1988 |
| JP | 2002-136086 | 5/2002 |
| JP | 2002-233575 | 8/2002 |

OTHER PUBLICATIONS

An article entitled "Magnetic Manipulation Instrumentation For Medical Physics Research", by Gillies et al., published at pp. 533 to 562 of *Rev. Sci. Instrum.* 65 (3), Mar. 1994.

An article entitled "EMR-Strip Biopsy For early Stages of Gastric", by Tada et al., which was published at pp. 782 to 783 of *Procedure of Strip Biopsy for early Gastric Cancer* (vol. 12, No. 6, 2000), along with a full English language translation.

(Continued)

*Primary Examiner*—Linda C. M. Dvorak
*Assistant Examiner*—Matthew J. Kasztejna
(74) *Attorney, Agent, or Firm*—Greenblum & Bernstein, P.L.C.

(57) ABSTRACT

A magnetic anchor remote guidance system includes an engagement member which engages with a body portion in a patient's body; a magnetic anchor made of a magnetic material, connected to the engagement member; and a magnetic anchor guide device which is disposed out of the patient's body and which produces a magnetic field to power the magnetic anchor. The body portion engaged by the engagement member is raised by supplying power to the magnetic anchor via the magnetic field produced by the magnetic anchor guide device.

18 Claims, 25 Drawing Sheets

OTHER PUBLICATIONS

An article entitled "Development Use of the POD Catheter in the Cerebral Vascular System", by Driller et al., which was published at pp. 11 to 16 of *Medical Research Engineering* (Aug./Sep. 1969).

An article entitled "Functional Design Features and Initial Performance Characteristics of a Magnetic-Implant Guidance System for Stereotactic Neurosurgery", by McNeil et al., which was published at pp. 793 to 801 of *IEEE Transactions On Biomedical Engineering* (vol. 42, No. 8, Aug. 1995).

* cited by examiner

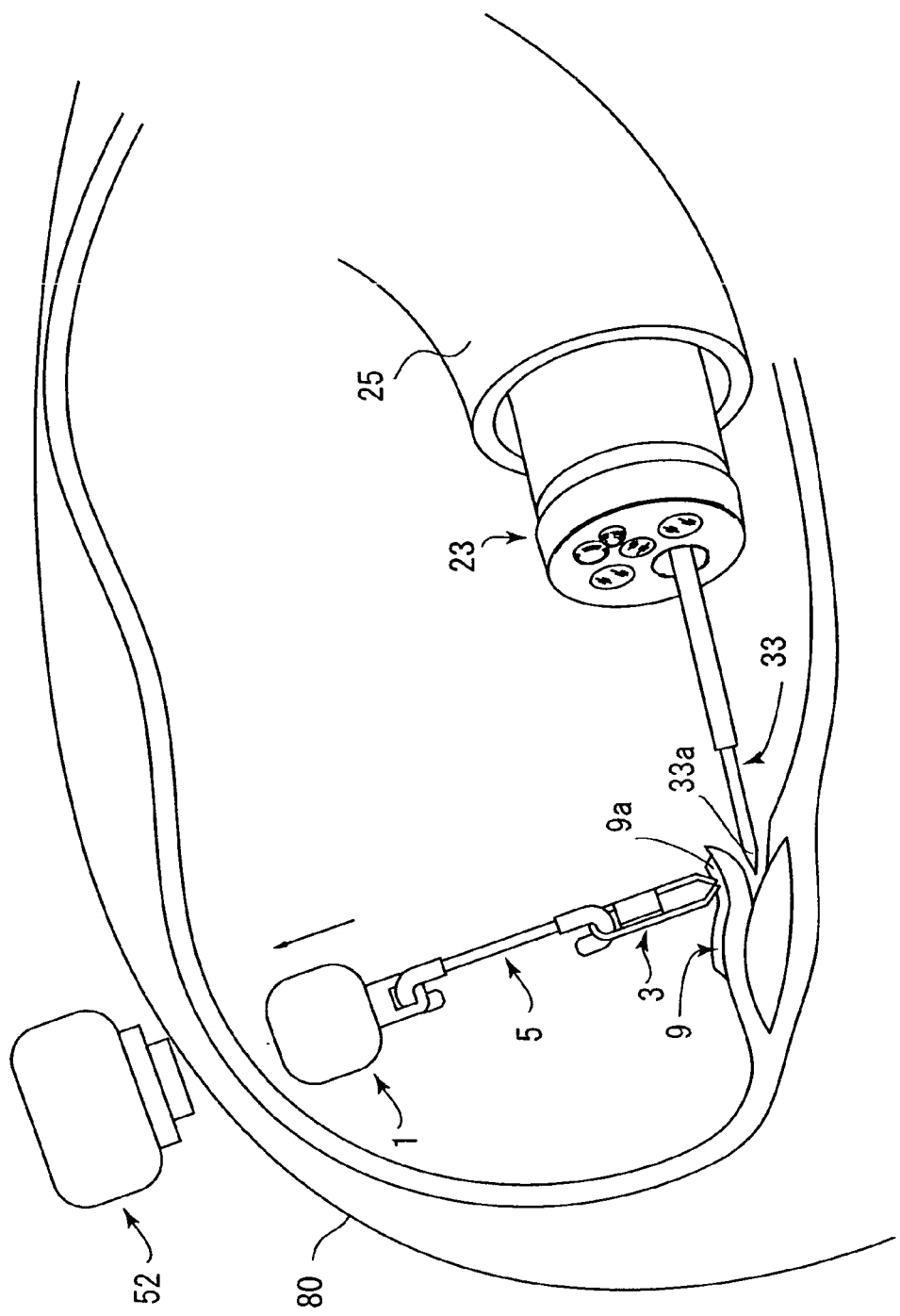

MAGNETIC ANCHOR REMOTE GUIDANCE SYSTEM

BACKGROUND OF THE INVENTION

1. Field of the Invention

The present invention relates to a magnetic anchor remote guidance system and a magnetic anchor guide apparatus, which can be used, for example, to resect a diseased portion (diseased portion), while observing the diseased portion through an endoscope.

2. Description of the Related Art

In general, in a surgical operation to resect a diseased portion inside a patient's body, the diseased portion is held and raised by forceps to increase the distance between the diseased portion and normal tissue adjacent thereto to thereby resect the portion between the diseased portion and the normal tissue. However, in an endoscopic mucosal resection (EMR), as only one endoscope can be inserted, it is impossible to raise the diseased portion using forceps. Therefore, a physiological saline is poured into the normal mucous membrane around the diseased portion through a syringe needle to raise the diseased portion. In this state, the portion between the diseased portion and the normal tissue is cut using a high frequency knife or snare, etc.

However, the amount of the diseased portion to be raised is small in the prior art and, hence, it is impossible to resect a sufficient amount of the boundary portion between the diseased portion and the normal tissue. Moreover, in case of the diseased portion being flat, it is sometimes impossible to provide a portion to be cut.

Furthermore, in the course of resection, the cut diseased portion tends to fall on the normal tissue and obstruct the field of view of the endoscope. This tendency is particularly apparent when the diseased portion is large. Therefore, the portion to be resected cannot be seen. Consequently, the resection is carried out blindly, and accordingly, the normal portion may be injured, thus leading to complications such as perforation, or blood vessels may get damaged, leading to heavy bleeding. If heavy bleeding occurs, hemostasis cannot be carried out due to the bleeding portion not being able to be visually confirmed, which could possibly lead to serious complications.

SUMMARY OF THE INVENTION

The present invention provides a magnetic anchor remote guidance system and a magnetic anchor guide apparatus used in the magnetic anchor remote guidance system, wherein the resection of a diseased portion can be quickly and easily carried out.

According to an aspect of the present invention, a magnetic anchor remote guidance system is provided, including an engagement member which engages with a body portion in a patient's body; a magnetic anchor made of a magnetic material, connected to the engagement member; and a magnetic anchor guide device which is disposed out of the patient's body and which produces a magnetic field to power the magnetic anchor. The body portion engaged by the engagement member can be raised by supplying power to the magnetic anchor via the magnetic field produced by the magnetic anchor guide device.

The engagement member can be a clip.

The engagement member can have a fishhook shape.

The magnetic anchor remote guidance system can further include a connector for connecting the magnetic anchor with the engagement member.

It is desirable for the connector to be extendible and contractible.

It is desirable for the magnetic anchor and the engagement member to be interconnected in advance.

The magnetic anchor guide device can include a magnetic guide member which produces the magnetic field to power the magnetic anchor made of a magnetic material; a two-dimensional moving mechanism which moves the magnetic guide member along a U-shaped frame which is arranged in a specific plane; and a unidirectional moving mechanism which relatively moves the U-shaped frame in a direction perpendicular to the plane.

The magnetic anchor guide device can include a magnetic guide member which produces the magnetic field to power the magnetic anchor made of a magnetic material; and an arm member which is supported on a main body which is movable on a surface of placement thereof, the arm being bendable at an articulated joint, so that the magnetic guide member is movable by adjusting the bending angle of the arm at the articulated joint.

The magnetic anchor guide device can be a plurality of magnetic guide devices in which the magnetic fields produced thereby are independently adjustable, so that the magnetic anchor can be powered by the resultant magnetic field of the magnetic guide devices.

The present disclosure relates to subject matter contained in Japanese Patent Application No. 2002-268239 (filed on Sep. 13, 2002) which is expressly incorporated herein by reference in its entirety.

BRIEF DESCRIPTION OF THE DRAWINGS

The invention will be discussed below in detail with reference to the accompanying drawings, in which:

FIG. 11 is a schematic view of a magnetic anchor guide apparatus according to the first embodiment of the present invention, when a diseased portion is resected using the same;

DESCRIPTION OF THE PREFERRED EMBODIMENTS (A) First Embodiment (I) Structure of Magnetic Anchor Remote Guidance System FIGS. 1 through 3 show the main elements (magnetic anchor 1, clip 3, and connector 5) of a magnetic anchor remote guidance system which are inserted in a patient's body. FIGS. 4 and 5 show a magnetic anchor guide apparatus 50 which attracts and controls (powers) the magnetic anchor 1 from the outside of the patient's body. FIGS. 6 through 10 show a magnetic anchor remote guidance system which is used to resect a diseased portion of a patient by way of example.

The magnetic anchor 1 includes a generally cylindrical ferromagnetic main body 1a which is provided on one surface thereof with a hole 1b. The ferromagnetic main body 1a can be a magnet made of, for example, fine iron or iron alloy, a platinum magnet, a rare-earth magnet, or a magnet made of terbium-disprosium-iron alloy, etc.

Figure 1:
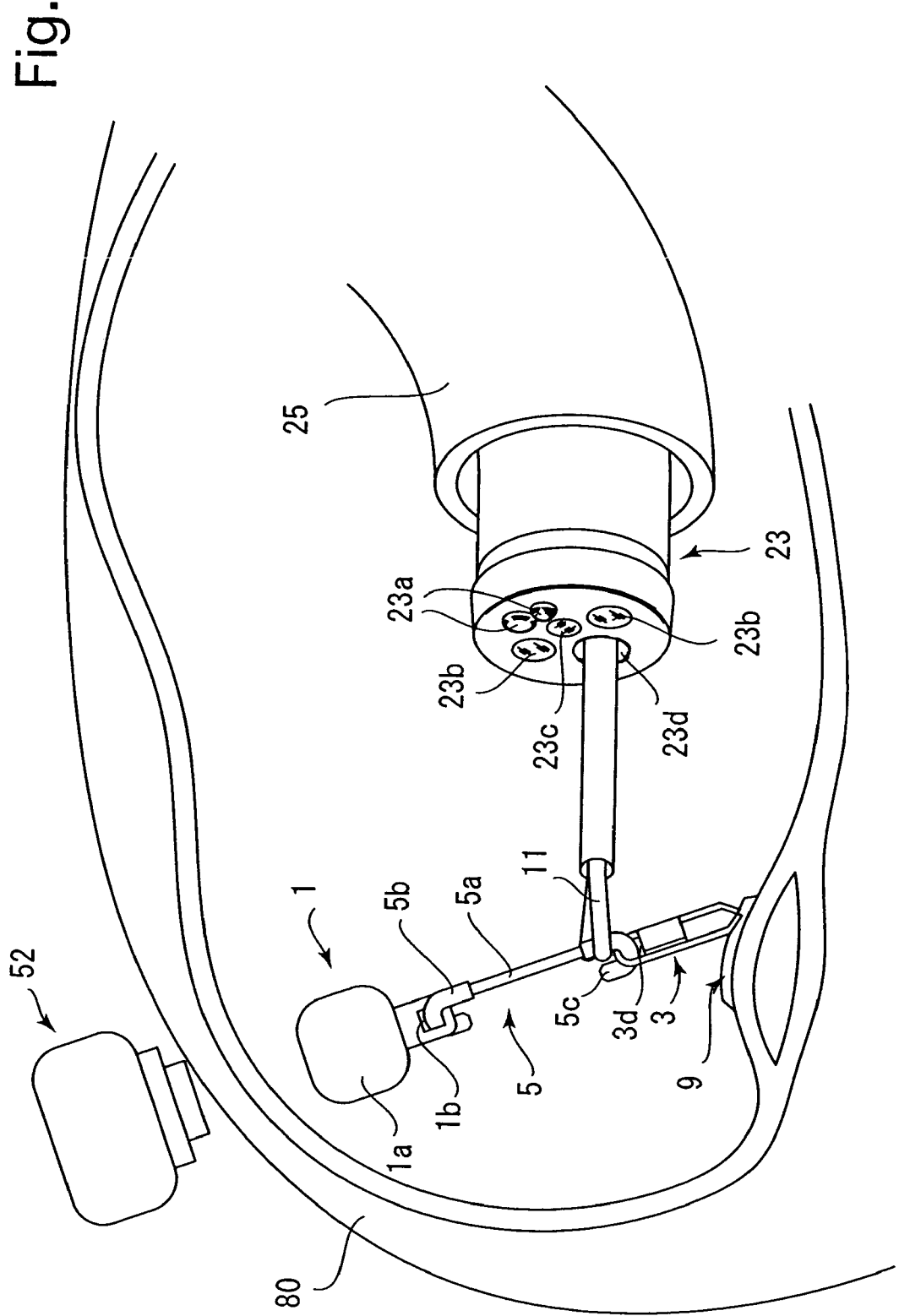
FIG. 1 is a schematic view of a structure of a magnetic anchor guide apparatus according to a first embodiment of the present invention.
Figure 2:
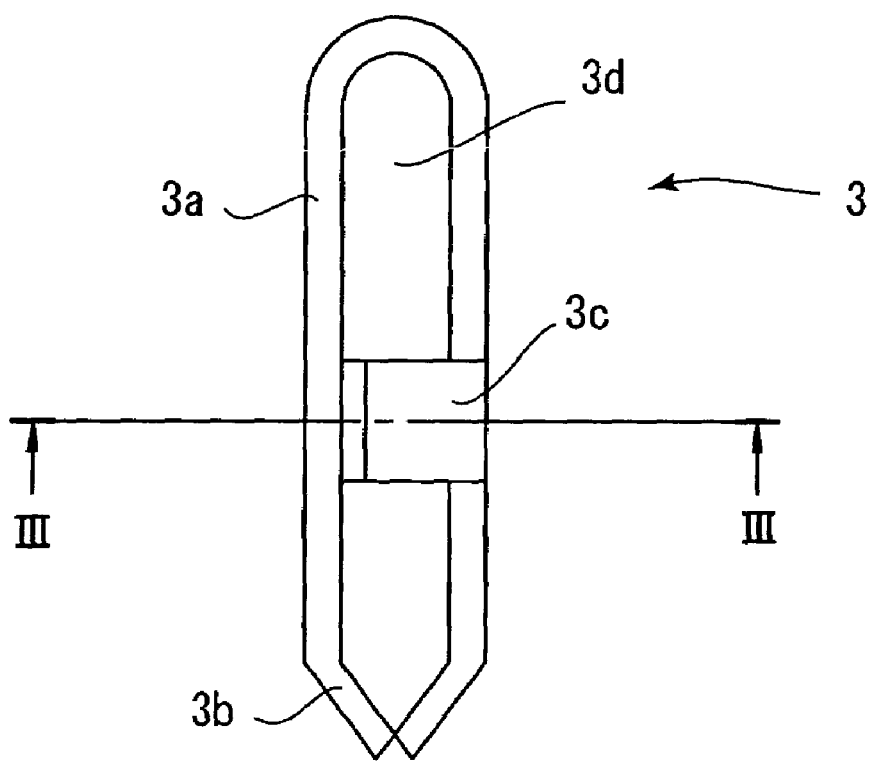
FIG. 2 is a view showing the shape of a clip in the first embodiment shown in FIG. 1.
Figure 3:
FIG. 3 is a sectional view taken along the line III—III in FIG. 2.

The clip 3 shown in FIGS. 2 and 3 defines an engagement member which is adapted to hold and raise a diseased portion (resection portion) 9 (FIG. 1) of a patient's body (subject). The clip 3 is provided with a generally U-shaped main body 3a having a pair of spaced arms with tip ends 3b having a variable distance (opening) 3d therebetween. The main body 3a is provided with a ratchet portion (distance adjusting portion) 3c which holds the opposed arms at an adjusted distance 3d. The ratchet portion 3c permits the opposed main bodies (arms) 3a to elastically deform in the direction to reduce the distance 3d and keeps the adjusted distance. In the initial state, the tip ends 3b of the clip 3 are spaced at a certain distance, due to the elasticity thereof.

The connector 5 connects the clip 3 to the magnetic anchor 1 and is provided with a pair of hooks 5b and 5c at opposed ends of the main body 5a. Connection is carried out by engaging the hooks 5b and 5c in the hole 1b of the magnetic anchor 1 and the hole 3d of the clip 3, respectively. The main body 5a can be made of a rigid, resilient or flexible material. For example, the main body 5a is made of a rubber or a spring. Alternatively, it is possible to provide length varying mechanisms on the hooks 5b and 5c, so that the length of the connector 5 can be adjusted. Note that it is also possible to directly connect the clip 3 to the magnetic anchor 1 or to integrally form the clip 3 with the magnetic anchor 1 without using the connector 5.

Figure 4:
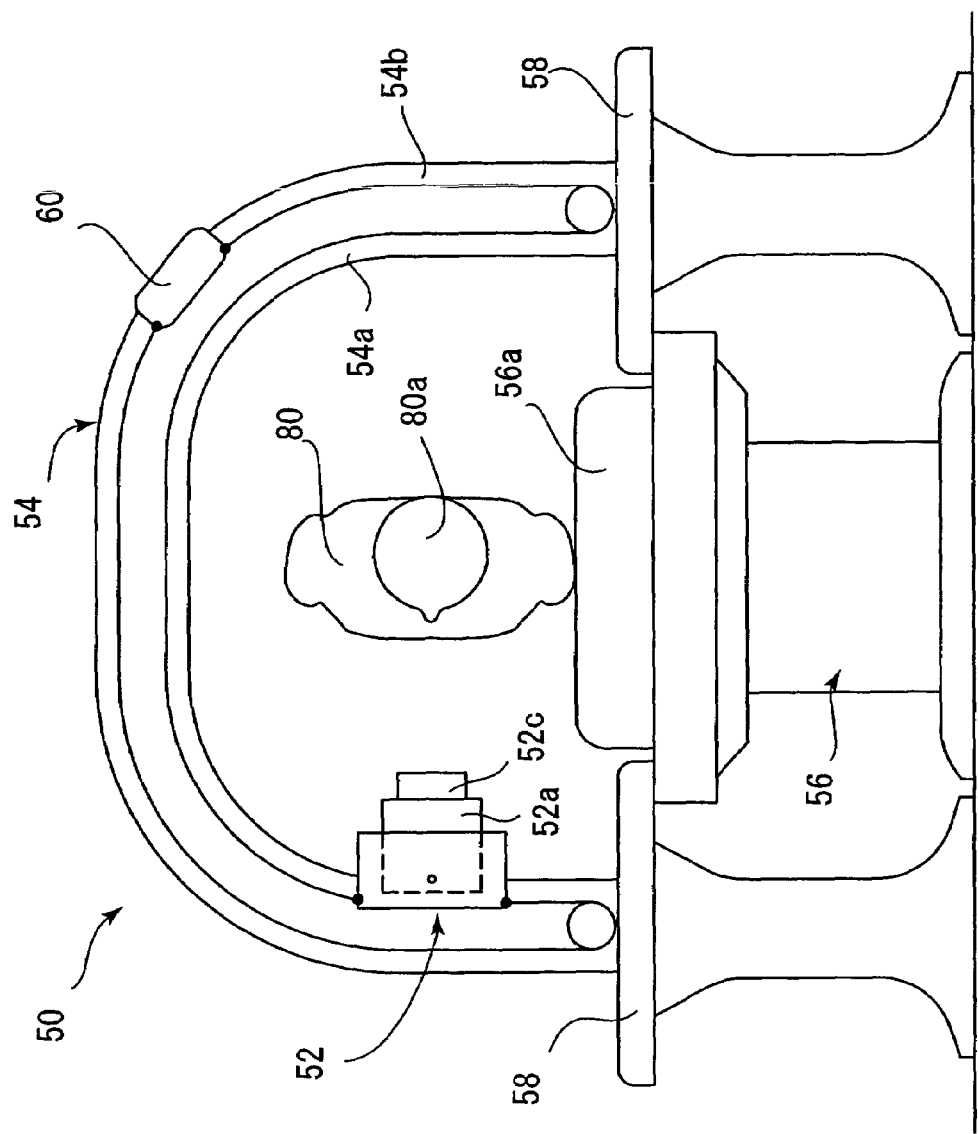
FIG. 4 is an end view of a bed on which a patient (whose diseased portion is to be resected) lies and an arrangement of magnetic guide members, viewed from the head side of the patient.

The magnetic anchor guide apparatus has a magnetic guide member 52 which attracts and controls (powers) the magnetic anchor 1 from the outside of the patient's body. As shown in FIG. 4, the magnetic guide member 52 includes a substrate 52a and an electromagnet 52c provided thereon, which is provided with an iron core wound by a coil. The magnetic guide member 52 can alternatively include a combination of a permanent magnet and an electromagnet, a combination of a plurality of permanent magnets and a plurality of electromagnets, a permanent magnet, or a combination of a plurality of permanent magnets.

Figure 5:
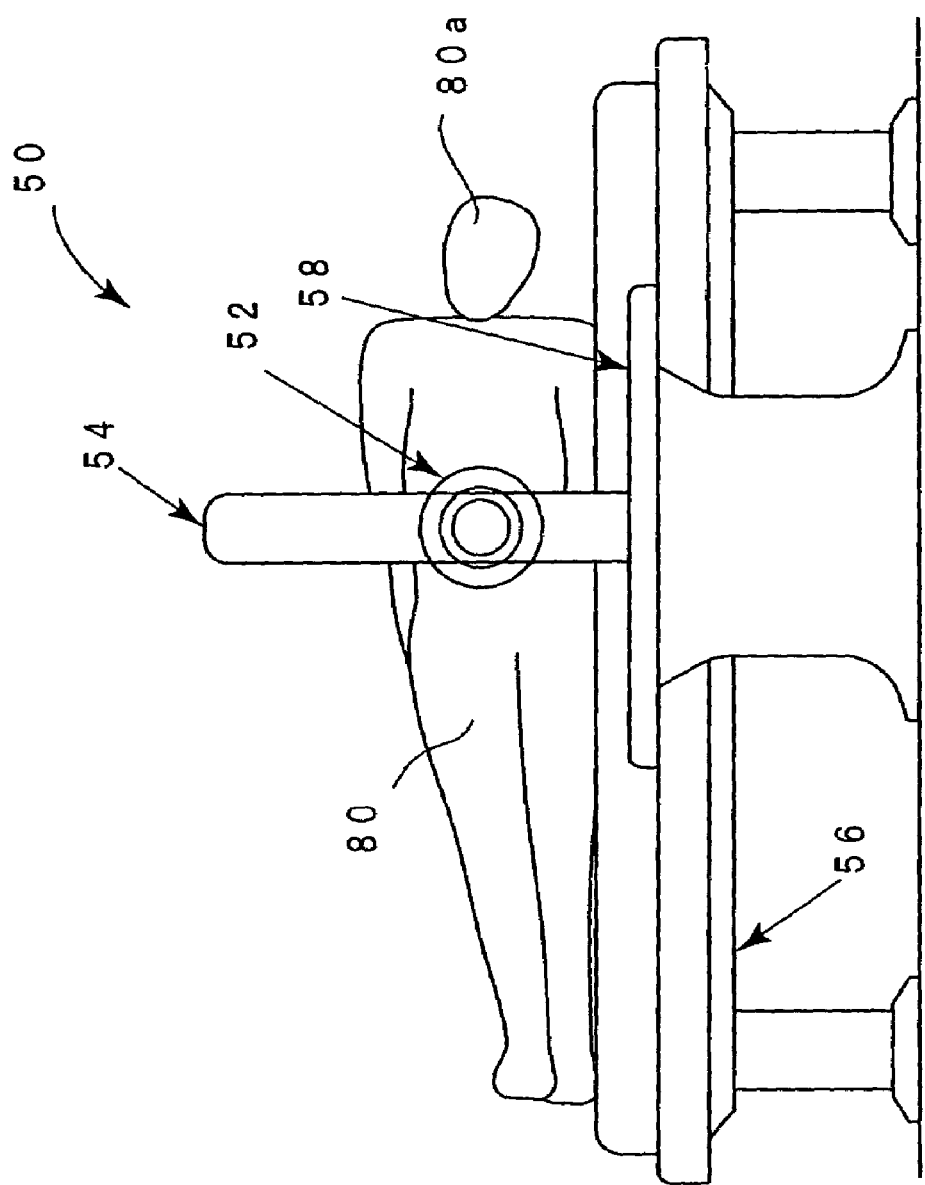
FIG. 5 is a front elevational view of a bed on which a patient (whose diseased portion is to be resected) lies and an arrangement of magnetic guide members.

The magnetic guide member 52 is slidably fitted on a frame/rail (uniplanar movement mechanism) 54 which is arranged to surround a bed 56 from above, on which a patient lies, as shown in FIGS. 4 and 5. The electromagnet 52c is opposed to the patient. The frame/rail 54 is composed of a pair of U-shaped rails 54a and 54b which extend in parallel in a plane, between two X-Y stages (unidirectional movement mechanism) 58 that extend in parallel with the width direction of a support plate 56a of the bed 56. The X-Y stages 58 are movable in a direction perpendicular to the plane in which the frame/rail 54 lies. Thus, the magnetic guide member 52 can be moved between the two X-Y stages 58 in accordance with the sliding movement of the substrate 52a along the frame/rail 54. The magnetic guide member 52 is provided on one of the parallel rails 54a and 54b of the frame/rail 54, i.e., the rail 54a which is located closer to the patient 80.

The rail 54b which is located away from the patient 80 compared to the rail 54a is provided with a counterweight 60 slidable thereon, which balances the weight of the entire the frame/rail 54. The position of the counterweight 60 is varied in accordance with the position of the magnetic guide member 52. For example, when the magnetic guide member 52 is located in a position to face the patient 80, the counterweight 60 is located behind the patient 80 and when the magnetic guide member 52 is located behind the patient 80, the counterweight 60 is located in a position to face the patient 80 in order to balance the weight of the entire the frame/rail 54.

The arrangement of the magnetic guide member 52, the X-Y stages 58, and the frame/rail 54, etc., as discussed above makes it possible to move the magnetic guide member 52 to the optimum position to resect the diseased portion 9. Therefore, it is possible to attract (or power) the magnetic anchor 1 and the clip 3 in order to raise the diseased portion to an appropriate resection position of the diseased tissue.

(2) Preparation for Resection Using Magnetic Anchor Remote Guidance System

To perform a resection using the magnetic anchor remote guidance system, the patient 80 who has been subjected to a local anesthesia lies on the bed 56. The frame/rail 54 is moved by the X-Y stages 58 to a retracted position close to the head 80a of the patient 80. The magnetic guide member 52 and the counterweight 60 are moved to predetermined positions. After the patient 80 lies on the bed 56, the frame/rail 54 is moved in front of the diseased portion of the patient by operating the X-Y stages 58 and thereafter, the magnetic guide member 52 is slid along the frame/rail 52 to a resection starting position.

(3) Insertion of Magnetic Anchor 1, Clip 3 and Connector 5 into Patient's Body

The magnetic anchor 1, the clip 3 and the connector 5 are inserted in the patient's body as follows.

FIGS. 6 through 9 show the insertion operation of the magnetic anchor guide apparatus 50 into the patient's body, according to a first embodiment of the present invention and show the distal end 23 of the endoscope at an enlarged size. No explanation of the structure of the endoscope will be given hereinafter. An outer tube 25 is inserted in advance in the patient's body, so that the insertion portion of the endoscope can be repeatedly inserted or removed through the outer tube 25. The distal end 23 of the insertion portion is provided with air and water supply nozzles 23a which supply air and clean water, upon resection of the diseased portion 9, an illumination window 23b through which the resection portion and the surroundings thereof are illuminated with illumination light, a view window 23c having an objective lens through which the resection portion and the surroundings can be viewed, and a forceps channel 23d.

The clip 3, the magnetic anchor 1 and the connector 5 are inserted in the patient's body through the forceps channel 23d.

Figure 6:
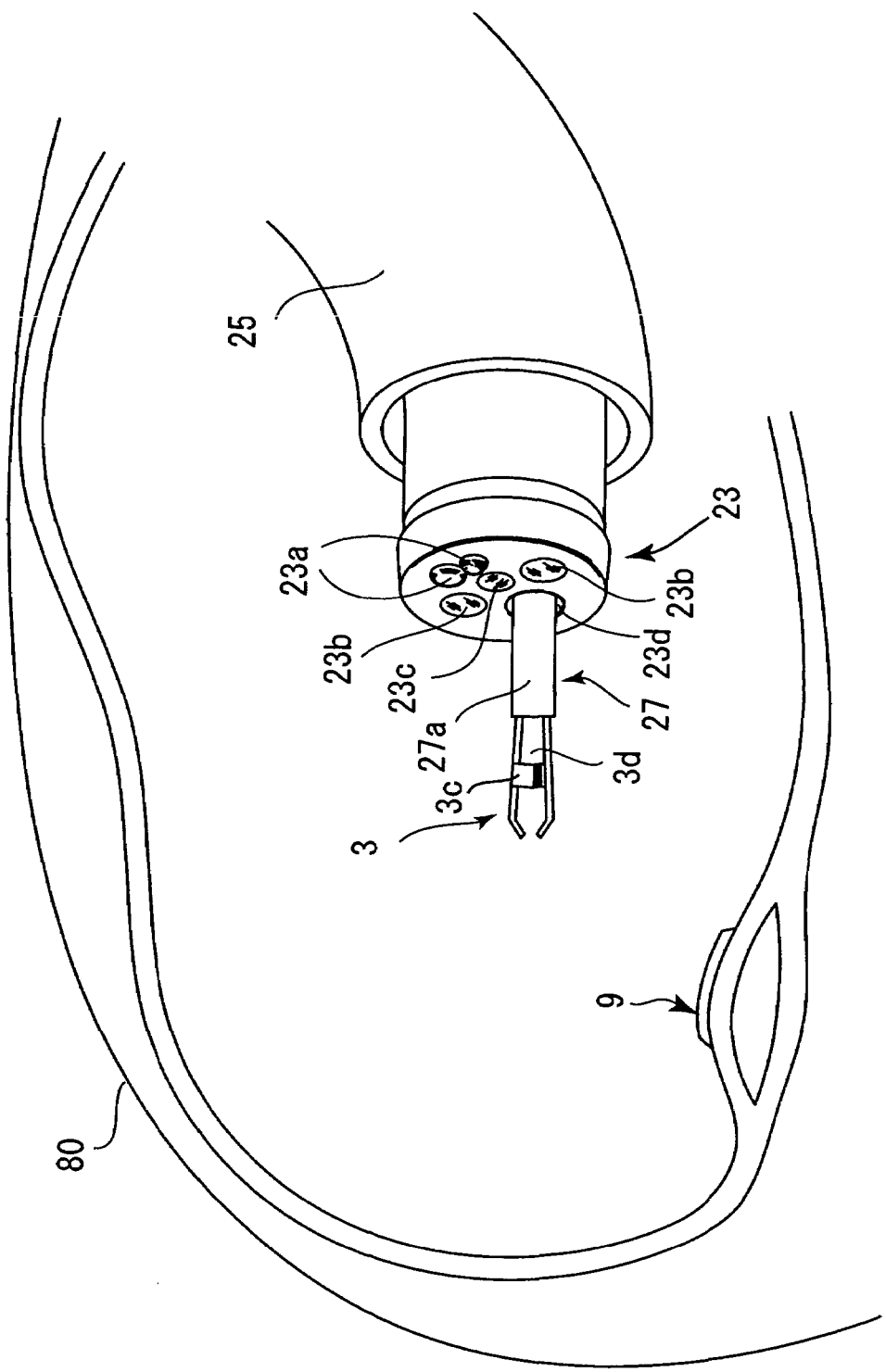
FIG. 6 is a schematic view of a magnetic anchor guide apparatus according to the first embodiment of the present invention, which is inserted in a patient's body.
Figure 7:
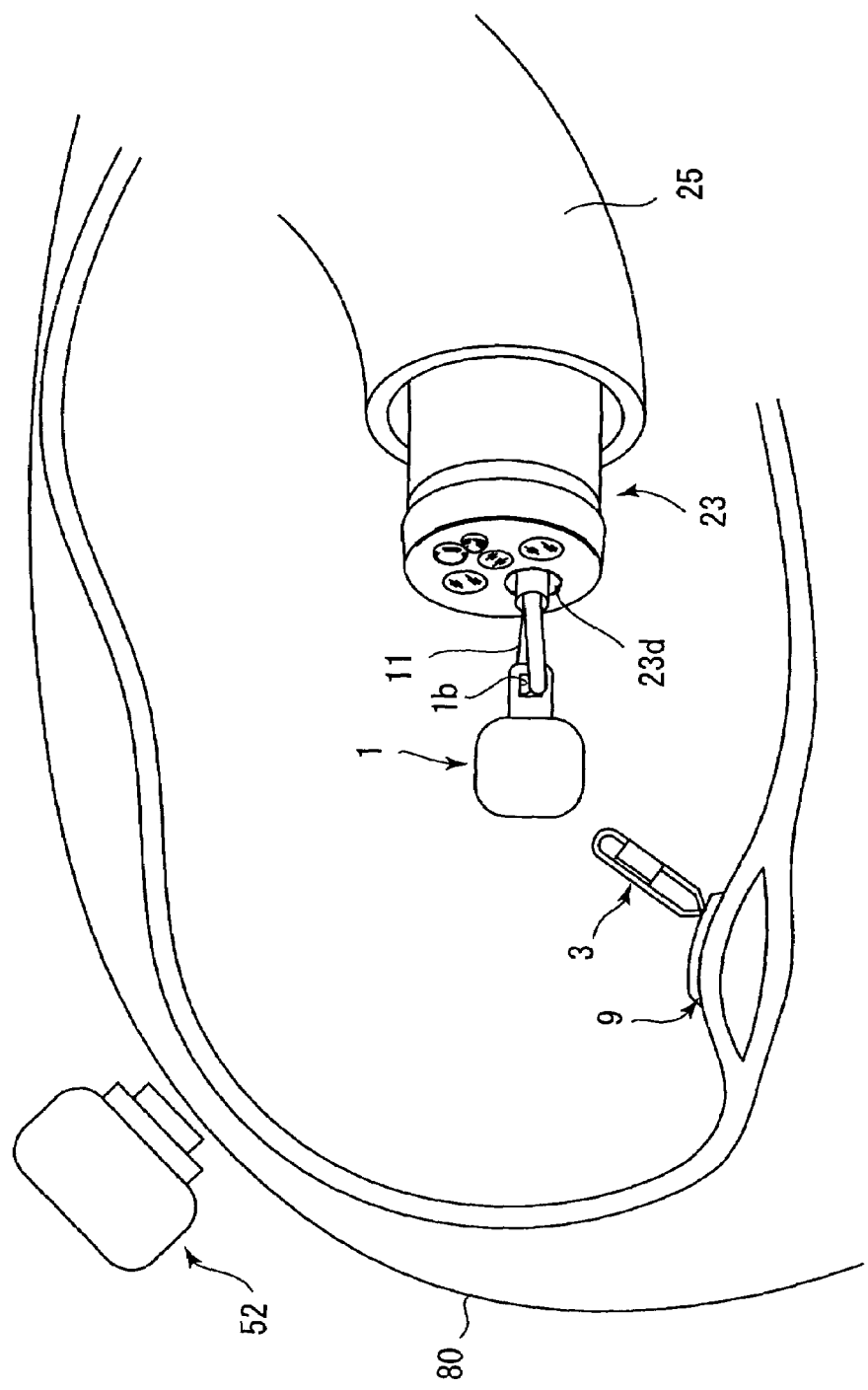
FIG. 7 is a schematic view of a magnetic anchor guide apparatus according to the first embodiment of the present invention, which is inserted in a patient's body.

As can be seen in FIGS. 6 and 7, the clip 3 is attached to the diseased portion 9 by a clip mounting tool 27. The clip mounting tool 27 is in the form of a flexible tube which is provided at its front end with a clamping portion 27a which holds and inserts the clip 3 in the patient's body. The clip 3 whose tip ends 3b are open is forced out of the clip mounting tool 27 by a pushing rod (not shown) which is inserted in the clip mounting tool 27 and is disposed in a desired position of the diseased portion 9. Thereafter, the clamping forceps 11 which is inserted in the forceps channel 23d is operated to fasten the distance adjusting portion 3c of the clip 3 to thereby close the tip ends 3d of the clip 3. Consequently, the diseased portion 9 is clamped by the clip 3.

Figure 8:
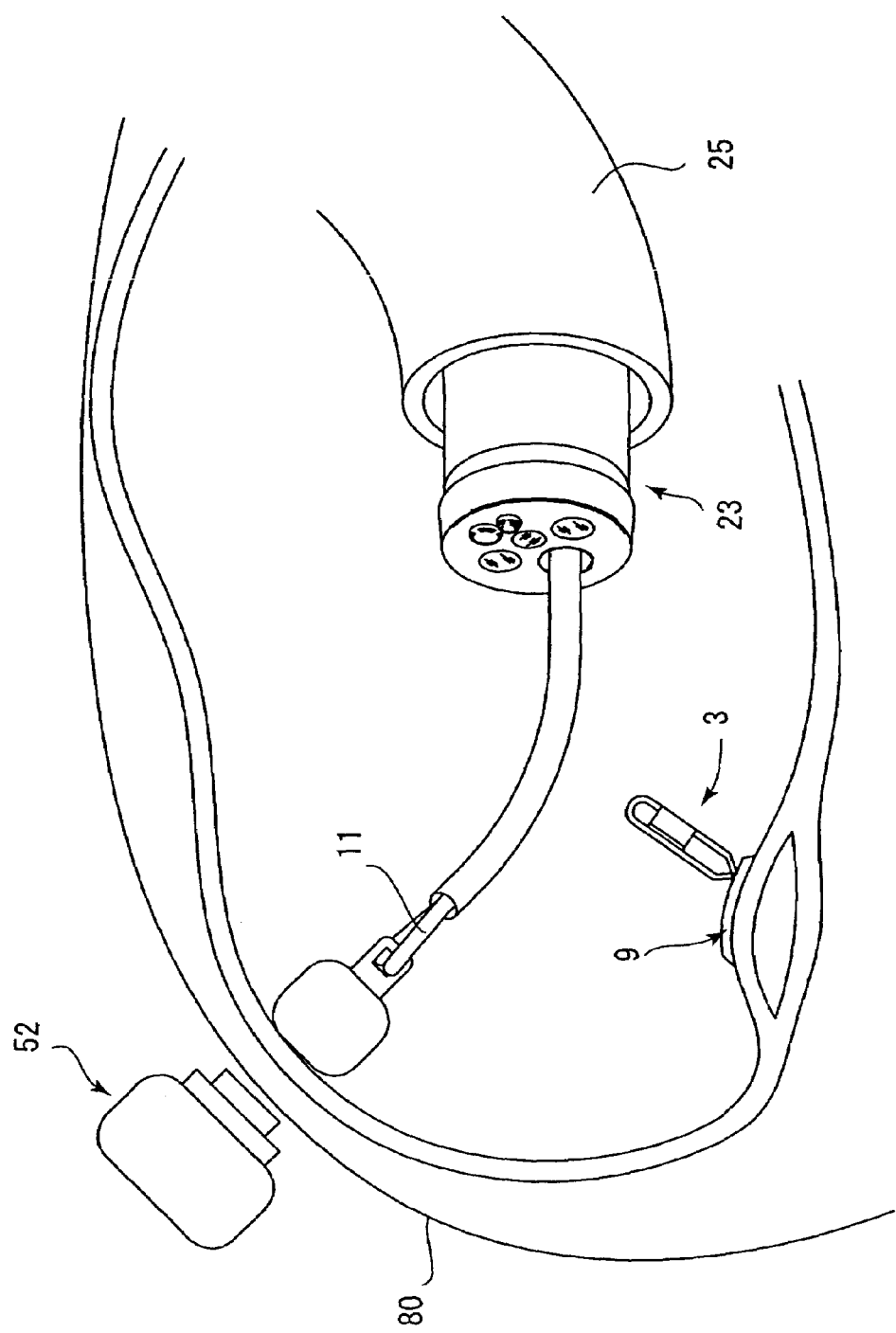
FIG. 8 is a schematic view of a magnetic anchor guide apparatus according to the first embodiment of the present invention, which is inserted in a patient's body.

As shown in FIG. 7, the magnetic anchor 1 is held at its hole 1b by the clamping forceps 11 inserted in advance in the forceps channel 23d and is inserted in the patient's body through the outer tube 25. As shown in FIG. 8, the magnetic anchor 1 is attracted by the magnetic guide member 52 which is arranged in advance in a desired position and is moved to a desired position in the patient's body. Note that the clip 3 may be disposed in the patient's body after the magnetic anchor 1 is disposed.

Figure 9:
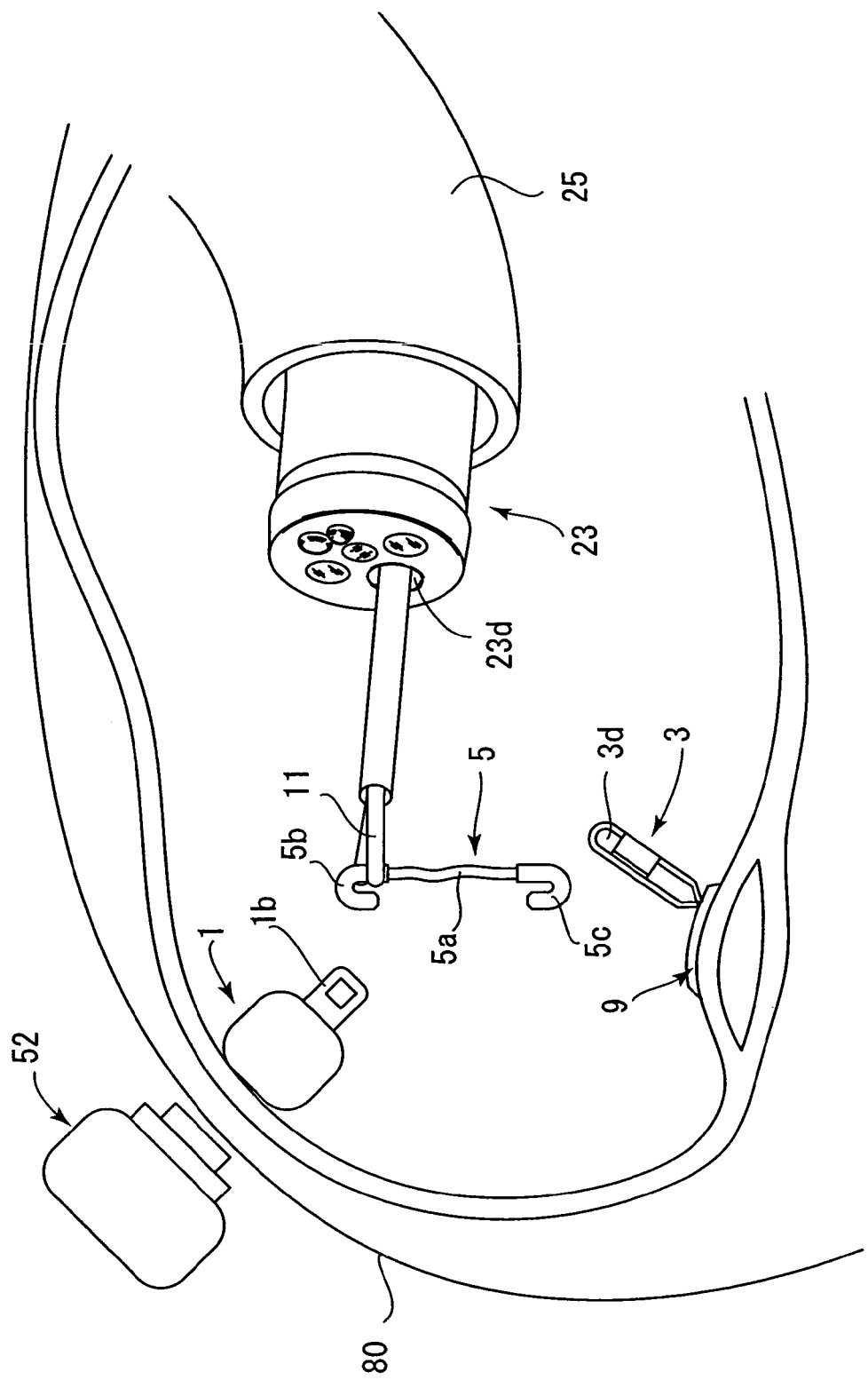
FIG. 9 is a schematic view of a magnetic anchor guide apparatus according to the first embodiment of the present invention, which is inserted in a patient's body.

As can be seen in FIG. 9, the connector 5 is engaged at the hook 5b with the clamping forceps 11 and is inserted in the patient's body through the forceps channel 23d. Thereafter, the hooks 5c and 5b of the connector 5 are engaged in the hole 3d of the clip 3 and the hole 1b of the magnetic anchor 1, respectively, by operating the clamping forceps 11. Consequently, the clip 3 and the magnetic anchor 1 are connected to each other. If the magnetic field produced by the magnetic guide member 52 is relatively weak, the operation mentioned above can be facilitated.

Thereafter, the length of the main body 5a of the connector 5 is varied by strengthening the magnetic field of the magnetic guide member 52, so that connector 5 is tightened when the clip 3 and the magnetic anchor 1 are connected by the connector 5 (FIG. 1). Thus, the movement of the magnetic guide member 52 can be easily transmitted to the clip 3 by adjusting the tension of the main body 5a of the connector 5 and, hence, a desired amount of the diseased portion 9 can be easily raised.

In the structure mentioned above, when the diseased portion 9 is resected, the tip ends 3b of the clip 3 which are open are pressed against the portion to be raised of the diseased portion 9. Thereafter, the distance adjusting portion 3c is gradually closed using the clamping forceps 11, so that the distance between the tip ends 3b of the clip 3 can be adjusted. The distance of the tip ends 3b of the clip 3 is reduced, so that the clip 3 clamps the diseased portion 9 at an appropriate pressure. In this state, the clamping forceps 11 is released from the distance adjusting portion 3c, and the adjusted distance of the tip ends 3b of the clip 3 is maintained by the ratchet mechanism of the distance adjusting portion 3c. Thus, when the clip 3 is moved upward, and the diseased portion 9 which is held by the clip 3 is raised.

In the magnetic anchor remote guidance system constructed as above, as the diseased portion 9 can be raised by a sufficient amount (height), a sufficient amount of the resection portion at the boundary between the diseased portion 9 and the normal tissue can be obtained. Therefore, a resection portion can be provided even if the diseased portion is flat. Moreover, since the clip 3 can be arranged at an optional position, the field of view of the endoscope is not obstructed by the cut diseased portion 9.

(4) Resection Step by Magnetic Anchor Remote Guidance System

Figure 10:
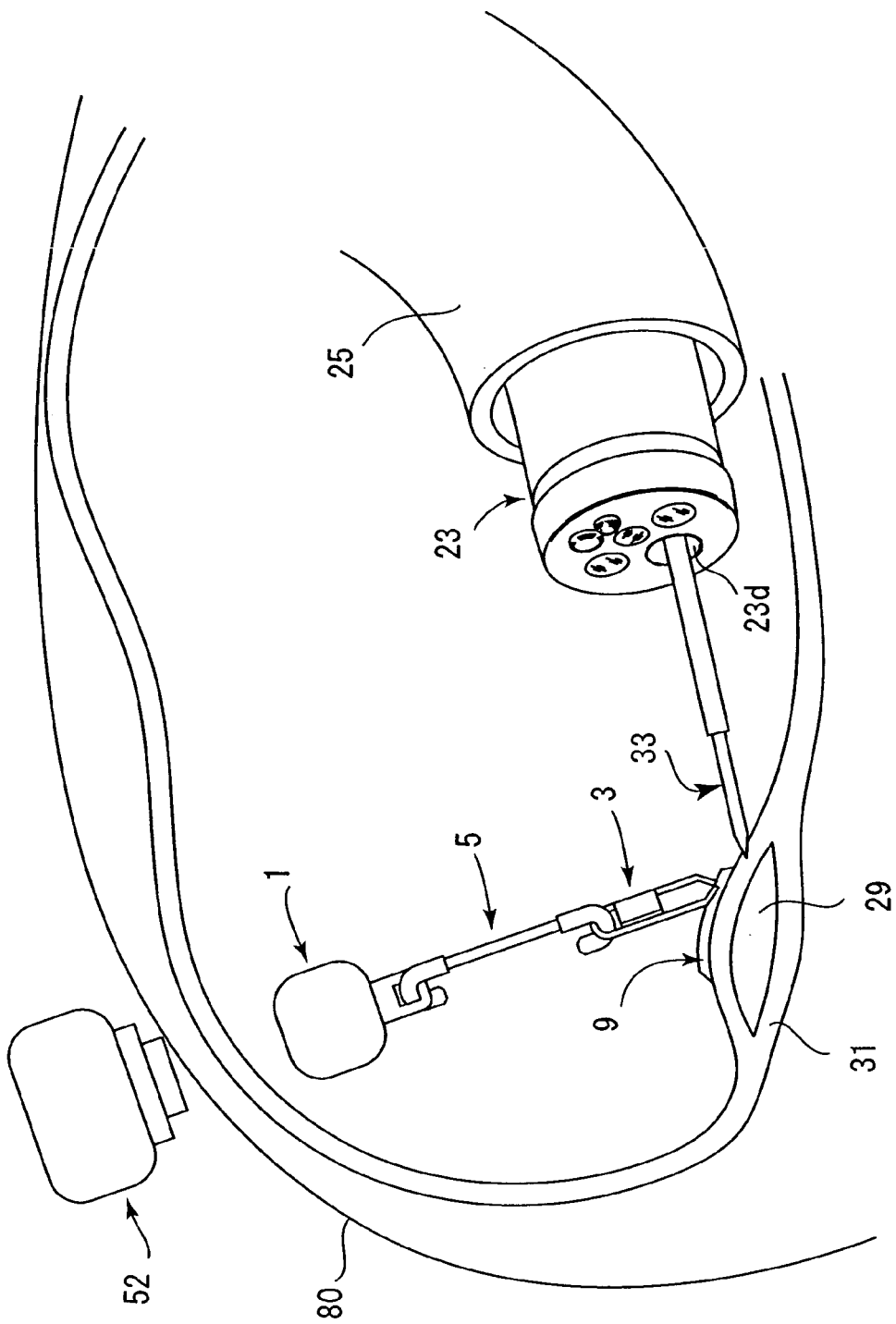
FIG. 10 is a schematic view of a magnetic anchor guide apparatus according to the first embodiment of the present invention, when a diseased portion is resected using the magnetic anchor guide apparatus.

The resection of the diseased portion 9 using the magnetic anchor remote guidance system constructed as above will be discussed below. FIGS. 10 and 11 show the resection operation of the diseased portion 9 by the use of the magnetic anchor guide apparatus 50, according to an embodiment of the present invention.

Firstly, a physiological saline is poured into a submucosal layer 29 through a syringe needle inserted in the submucosal layer from the vicinity of the diseased portion 9 to raise the diseased portion 9 from the proper muscular tunics 31. Furthermore, the magnetic guide member 52 is placed in a predetermined position near the diseased portion 9. In this state, the clip 3 is set in the optimum position to resect the diseased portion 9. Thereafter, the magnetic anchor 1 is set through the connector 5. Consequently, the diseased portion 9 is raised due to the magnetic attraction between the magnetic guide member 52 and the magnetic anchor 1. If the amount of the raise is too large or insufficient, the amount is adjusted by moving the magnetic guide member 52 or weakening the magnetic field produced by the magnetic guide member 52. If the position of the clip 3 is not appropriate, the clip 3 is detached and re-attached to an appropriate position by the clamping forceps 11 while the magnetic field of the magnetic guide member 52 is weakened.

Thereafter, a dissector, such as a high-frequency scalpel 33, is inserted in the patient's body through the forceps channel 23d to resect the diseased portion 9 together with the mucous membrane at the end portion 9a (see FIG. 11). As the diseased portion 9 is raised by the clip 3, a sufficient amount of the resection portion can be provided, so that there is no chance of the cut diseased portion 9 falling on the proper muscular tunics 31. Moreover, it is possible to further raise the cut diseased portion 9 by gradually moving the magnetic guide member 52, and accordingly, the position of the tip end 33a of the high-frequency scalpel 33 can be easily confirmed, thus resulting in a smooth resection operation.

When the resection is completed, the magnetic anchor 1 is attracted by the magnetic guide member 52 while the cut diseased portion 9 is attached to the clip 3. Therefore, there is no possibility that the diseased portion 9 is lost. To recover the cut diseased portion 9, while the magnetic anchor 1, the clip 3, the connector 5 and a part of the cut diseased portion 9 are engaged by the clamping forceps 11, the supply of the electricity to the magnetic guide member 52 is stopped and the endoscope is removed. Thereafter, the operations, such as suture or disinfection are carried out.

(B) Second Embodiment

Figure 12A:
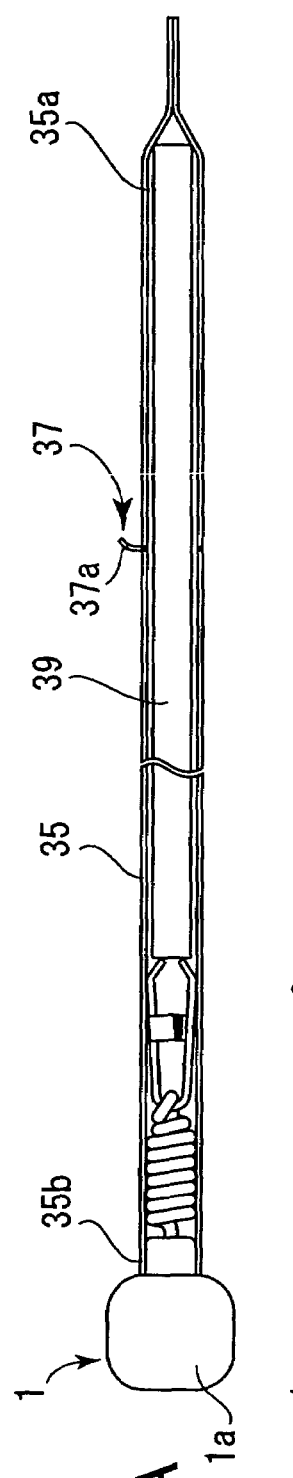
FIG. 12A is a view of a magnetic anchor, a connector, and a clip set in a guide sheath.
Figure 12B:
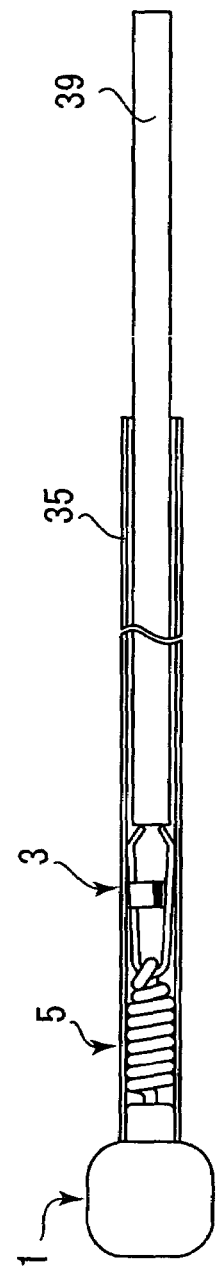
FIG. 12B is a view of a guide sheath whose rear end portion is removed by pulling a cutting string.
Figure 12C:
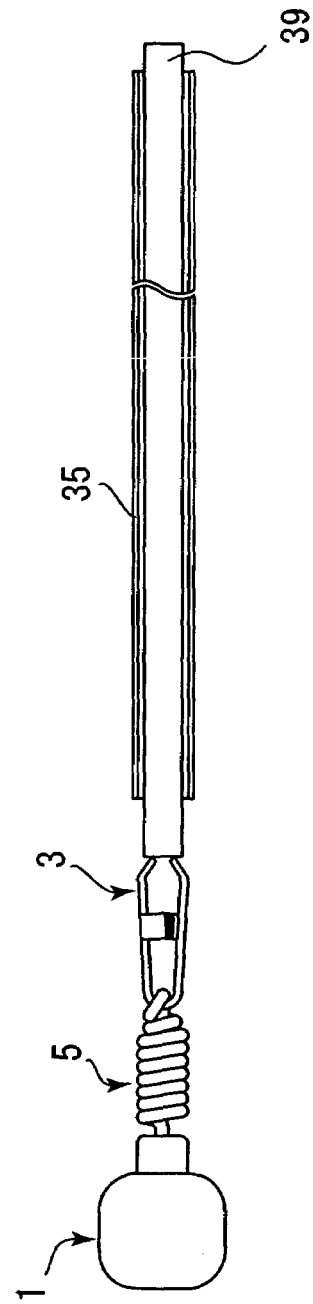
FIG. 12C is a view of a magnetic anchor, a connector, and a clip, forced out of a guide sheath by pushing a flexible pushing rod.

FIGS. 12A through 12C show a relationship of the magnetic anchor 1, the connector 5, the clip 3 and the guide sheath 35 according to the second embodiment of the present invention. Note that in the second embodiment, the elements corresponding to those in the first embodiment are designated with like reference numerals.

Figure 13:
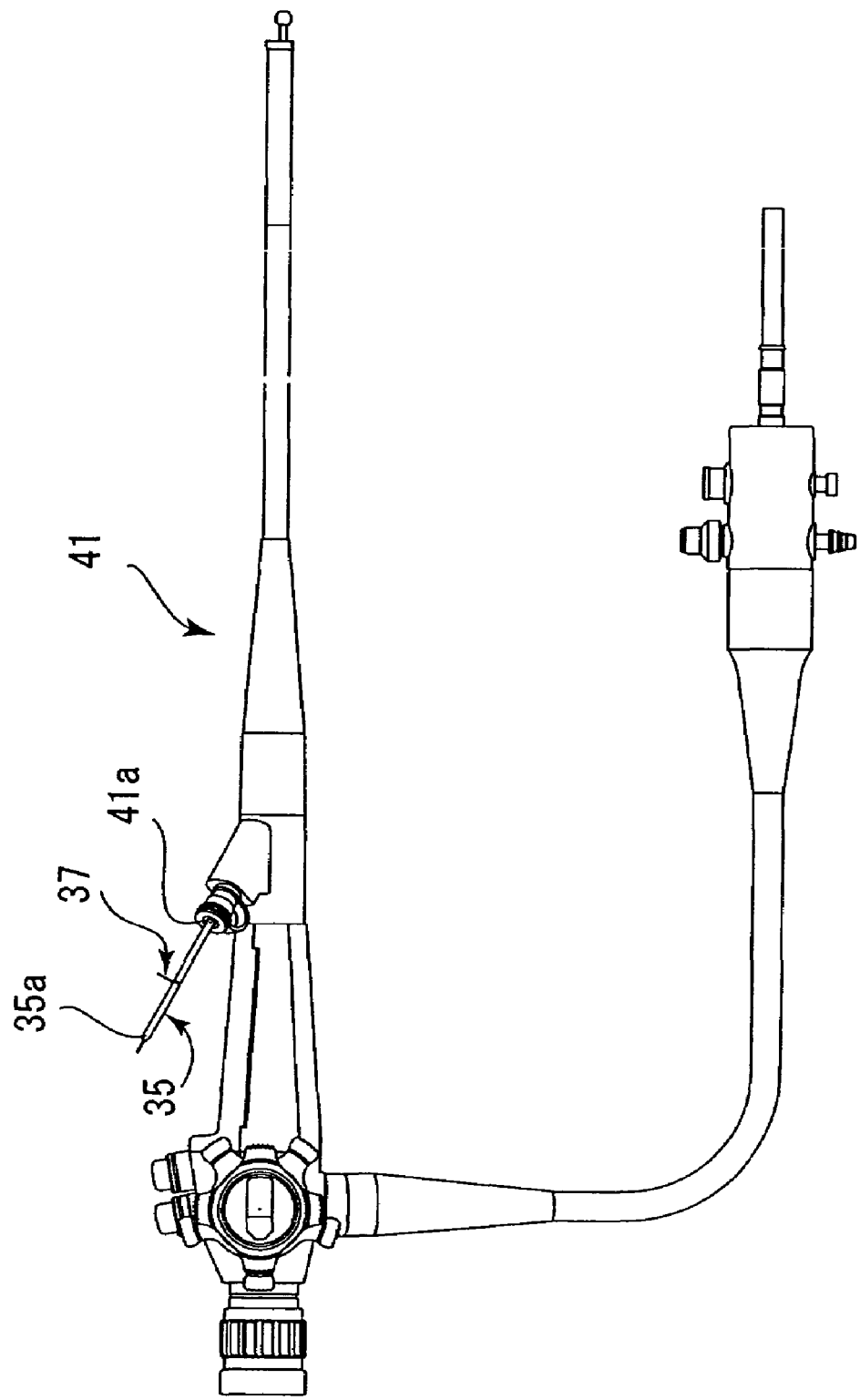
FIG. 13 is a view of an endoscope having a magnetic anchor, a connector and a clip, according to a second embodiment of the present invention.

In the second embodiment, the magnetic anchor 1, the connector 5, and the clip 3 are inserted integrally in the patient's body. FIG. 12A shows a position in which the magnetic anchor 1, the connector 5 and the clip 3 are set in the guide sheath 35. FIG. 12B shows a position in which the rear end 35a of the guide sheath 35 has been removed by pulling a cutting string 37 of FIG. 12A. FIG. 12C shows a position in which the magnetic anchor 1, the connector 5 and the clip 3 are forced out of the guide sheath by pushing a flexible pushing rod 39. FIG. 13 shows an outer appearance of the endoscope 41 in which the magnetic anchor 1, the connector 5 and the clip 3 are set, according to the second embodiment of the present invention.

Upon introduction of the endoscope, the magnetic anchor 1, the connector 5 and the clip 3 are integrally connected and are inserted in the guide sheath 35 in the form of a flexible hollow tube. Only the main body 1a of the magnetic anchor 1 is located outside of the tip end 35b of the guide sheath 35. The hole 1b of the magnetic anchor 1, the connector 5 connected thereto and the clip 3 connected to the connector 5 are located in the guide sheath 35. The tip ends 3b of the clip 3 abut against the flexible pushing rod 39 in the guide sheath 35. The flexible pushing rod 39 extends over the entire length of the guide sheath 35 whose rear end 35a is welded. The guide sheath 35 is longer than the length from the tip end 23 of the endoscope 41 to the forceps insertion opening 41a. Therefore, when the guide sheath 35 is set in the endoscope 41, with the main body 1a of the magnetic anchor 1 protruding from the distal end 23 of the endoscope 41, the rear end 35a of the guide sheath 35 is located out of the forceps insertion opening 41a.

The rear end 35a of the guide sheath 35 projecting from the forceps insertion opening 41a is provided with the cutting string 37. The cutting string 37 extends in the circumferential direction of the guide sheath 35. The outer end 37a of the cutting string 37 extends outwardly away from the guide sheath 35, so that an operator can easily hold and pull the outer end 37a of the string 37. The remaining portion of the cutting string 37 other than the outer end 37a is integral with the guide sheath 35. When an operator pulls the cutting string 37, the latter is removed along the circumferential direction of the guide sheath 35. Consequently, the guide sheath 35 is split into two in the axial direction at the portion thereof from which the cutting string 37 has been removed. When the rear end 35a of the guide sheath 35 is drawn and removed, the flexible pushing rod 39 provided in the guide sheath 35 is exposed. The movement of the flexible pushing rod 39 in the axial direction causes the magnetic anchor 1, the connector 5 and the clip 3 to be forced out from the front end of the guide sheath 35 into the patient's body.

Figure 14:
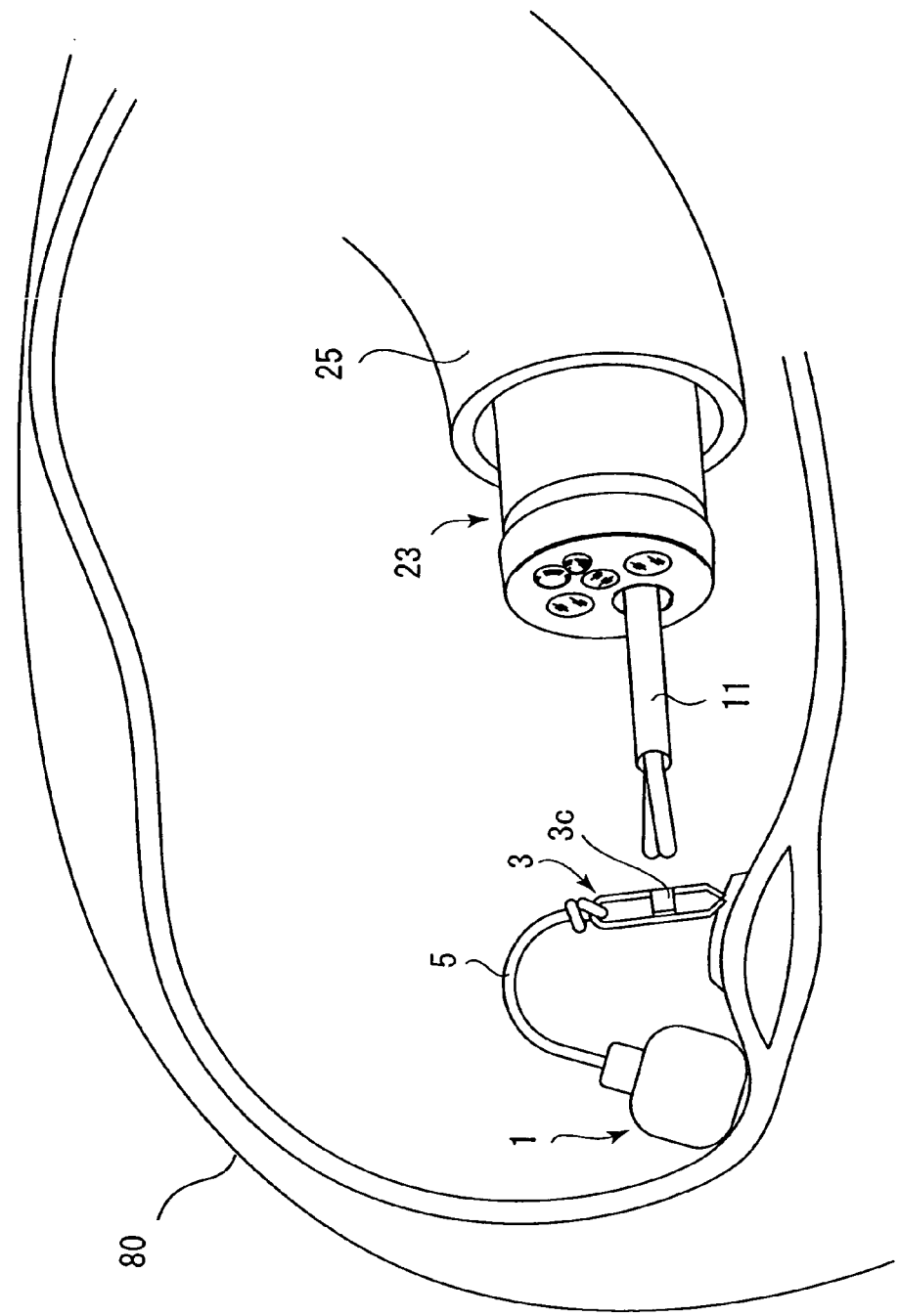
FIG. 14 is a schematic view of a magnetic anchor, a connector and a clip, introduced in a patient's body.
Figure 15:
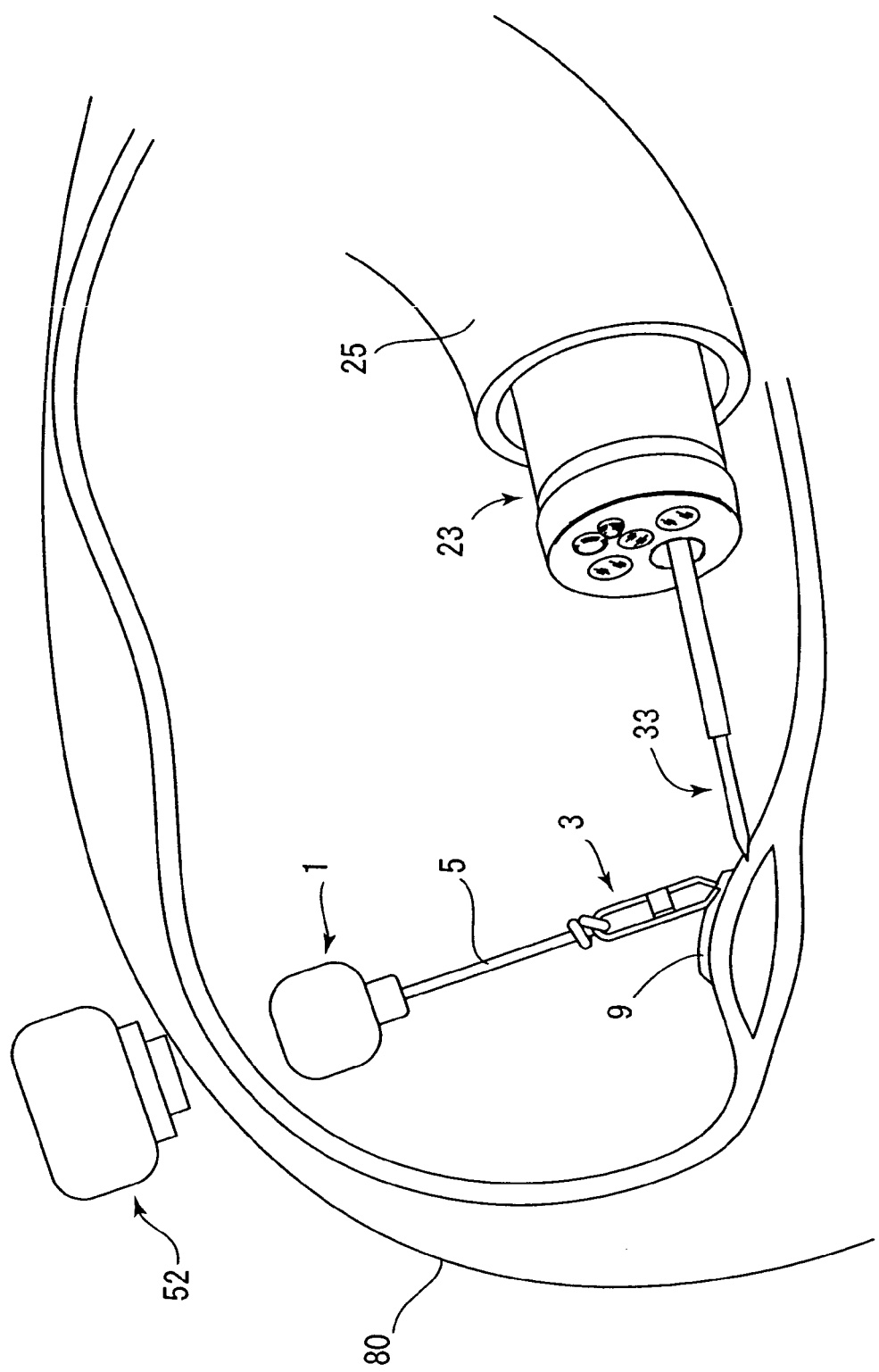
FIG. 15 is a schematic view of a magnetic anchor which is attracted by a magnetic guide member.

FIG. 14 shows the magnetic anchor 1, the connector 5 and the clip 3, inserted in the patient's body. FIG. 15 shows the magnetic anchor 1 which is attracted (or powered) by the magnetic guide member 52. Regarding the magnetic anchor 1, the connector 5 and the clip 3, introduced in the patient's body, the clip 3 is arranged in a predetermined position by the use of the clamping forceps 11, and thereafter, the distance adjusting portion 3c is fastened by the clamping forceps 11 to close the tip ends 3b of the clip 3. In this state, the magnetic field produced by the magnetic guide member 52 is set to be weak. Subsequently, the quantity of electricity supplied to the coil of the magnetic guide member 52 is increased to enhance the magnetic field produced thereby. As a result, the magnetic anchor 1 is magnetically attracted to raise the diseased portion 9 to a desired height. The remaining structure, other operations and effects of the second embodiment are the same as those in the first embodiment.

Figure 16:
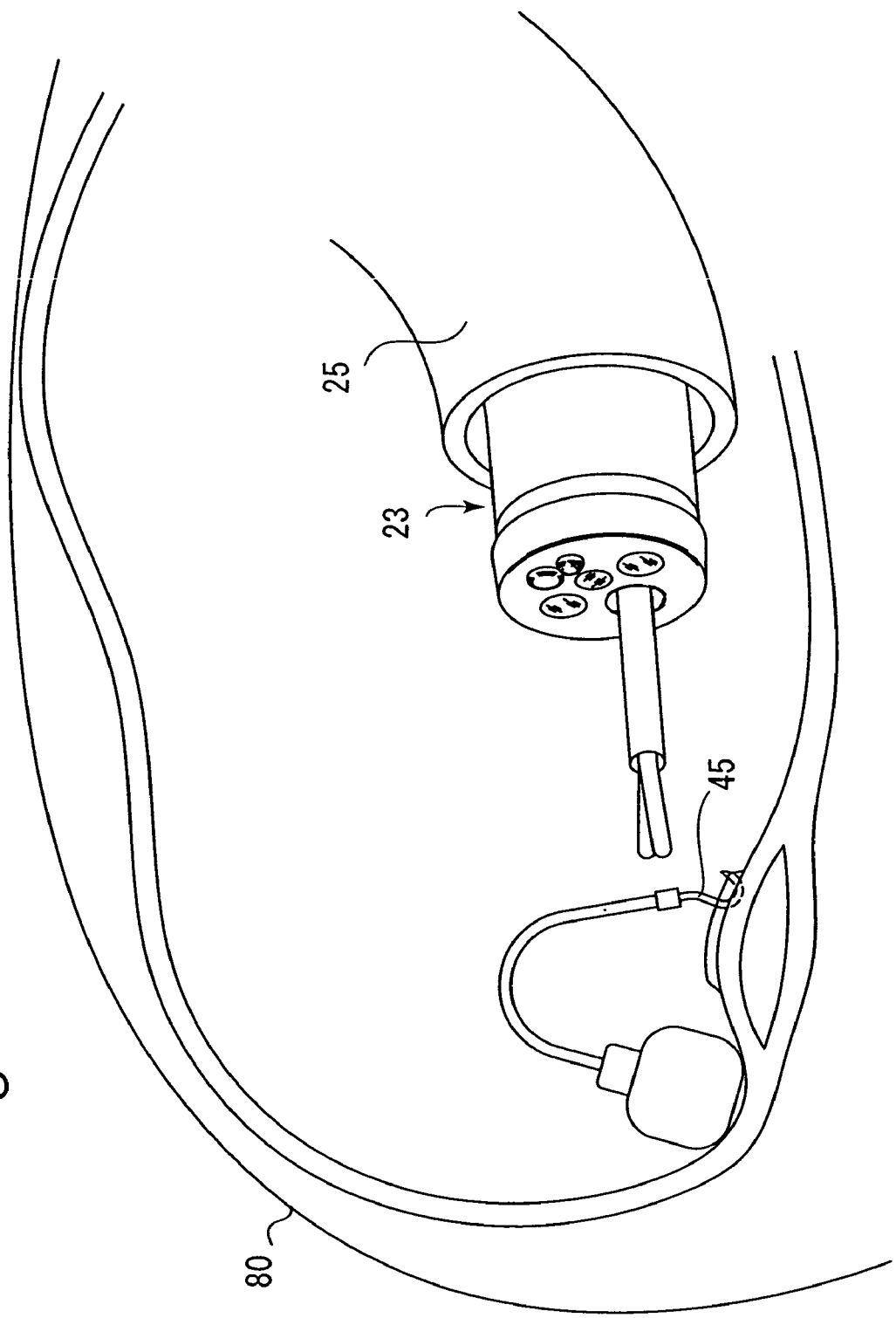
FIG. 16 is a view of an apparatus using a fishhook-shaped engagement member according to the second embodiment of the present invention.

FIG. 16 shows a modification of the engagement member, in which the clip 3 is replaced with a fishhook-shaped engagement member 45. The fishhook-shaped engagement member 45 is hooked and fastened into the diseased portion. The fishhook-shaped engagement member 45 can be more easily connected to the diseased portion than the clip 3.

(C) Third Embodiment

Figure 17:
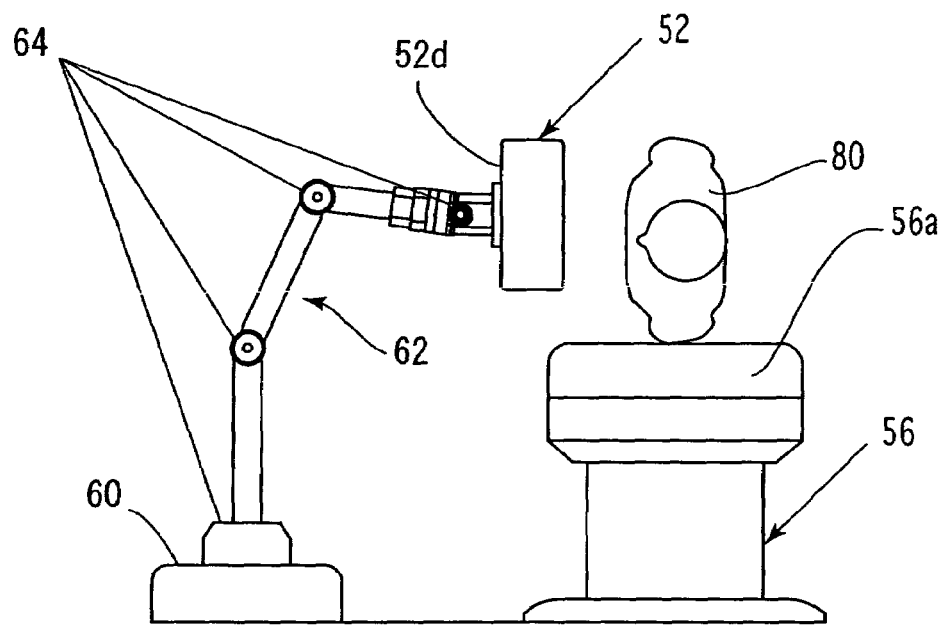
FIG. 17 is a view of a magnetic anchor guide apparatus according to a third embodiment of the present invention.

In the third embodiment of the invention, the magnetic guide member 52 located in front of the patient 80 is supported at the back 52d thereof by an arm 62 which is supported by a main body 60 capable of moving in a plane, as show in FIG. 17. The arm 62 is provided with three articulated joints 64 so that the arm 62 is rotatable at the articulated joints in the longitudinal direction of the arm. The rotatable magnetic guide member 52 can be moved to an optional position on the front side of the patient 80 by moving the main body 60 and independently adjusting the rotational angle of the arm at the articulated joints 64. The remaining structure, other operations and effects of the third embodiment are the same as those of the first embodiment. The number and position of the articulated joints 64 are optional. The direction of the movement of the arm at the articulated joints is not limited to the longitudinal direction of the arm and is optional. Moreover, the arm 62 may be secured to the main body 60 or may be rotatably supported by the main body 60. Furthermore, the arm 62 may be extendible and contractible.

(D) Fourth Embodiment

Figure 18:
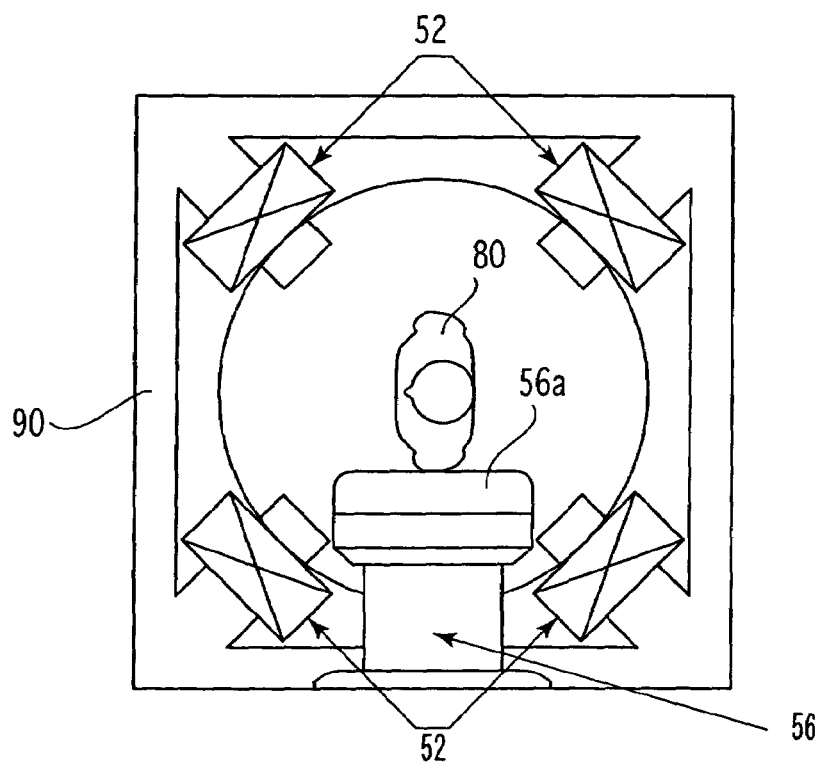
FIG. 18 is a view of a magnetic anchor guide apparatus according to a fourth embodiment of the present invention.

In the fourth embodiment, as shown in FIG. 18, four magnetic guide members 52 are provided on an inner wall of a box frame 90 which surrounds the patient 80 at the upper corners and lower corners of the box frame 90, so that the magnetic guide members 52 are diagonally opposed to each other and obliquely opposed to the patient. The resultant magnetic field produced by the four magnetic guide members 52 can be controlled by independently controlling the electric current supplied to the magnetic guide members 52. Thus, the intensity and direction of the resultant magnetic field can be optionally adjusted, and hence, it is possible to move the magnetic anchor 1 and the clip 3 arranged in the patient's body 80 in an optional direction and to a desired height due to the magnetic attraction.

Figure 19:
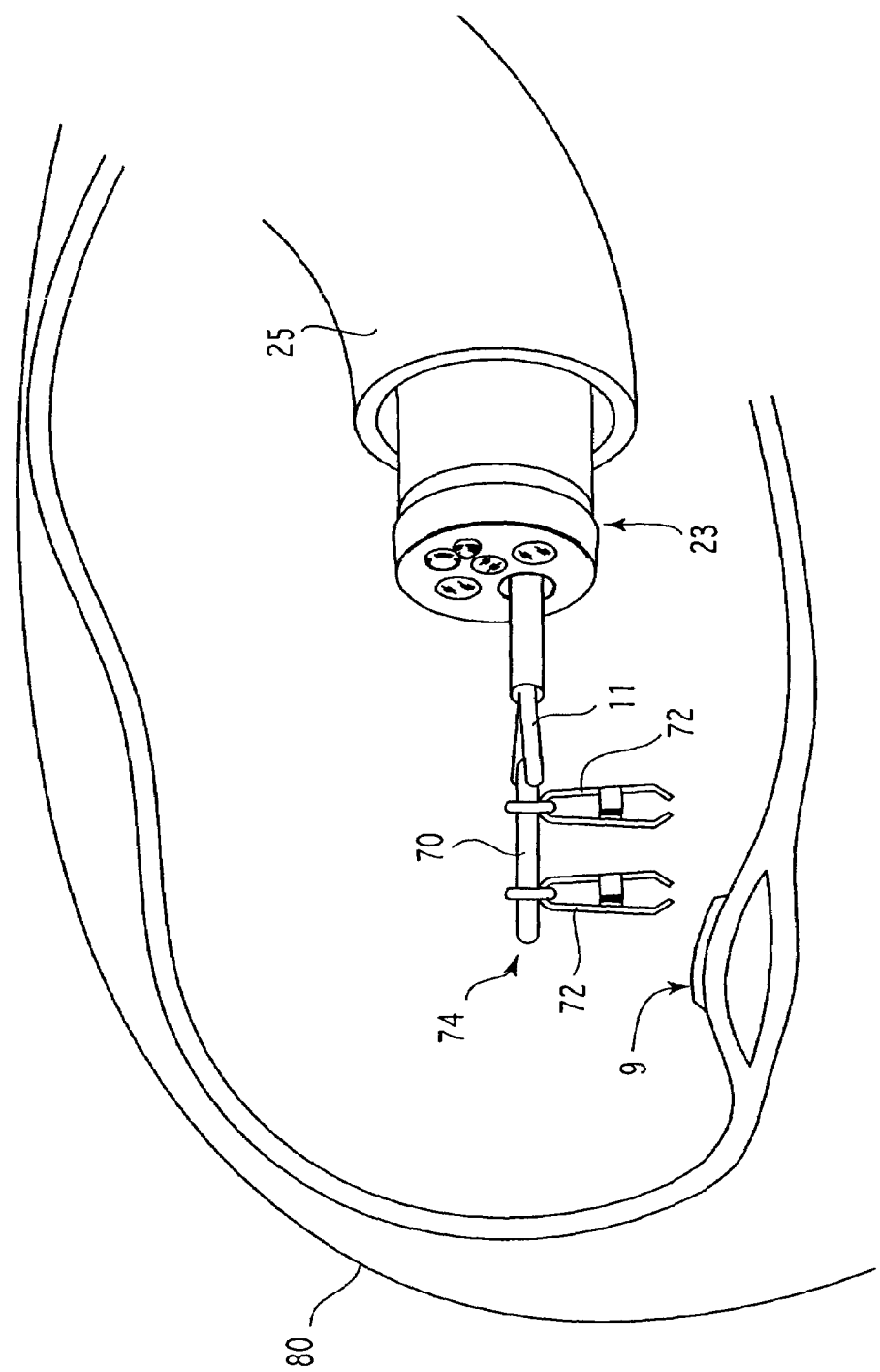
FIG. 19 is a view of a magnetic anchor guide apparatus using an engagement member according to a modification of the fourth embodiment of the present invention.
Figure 20:
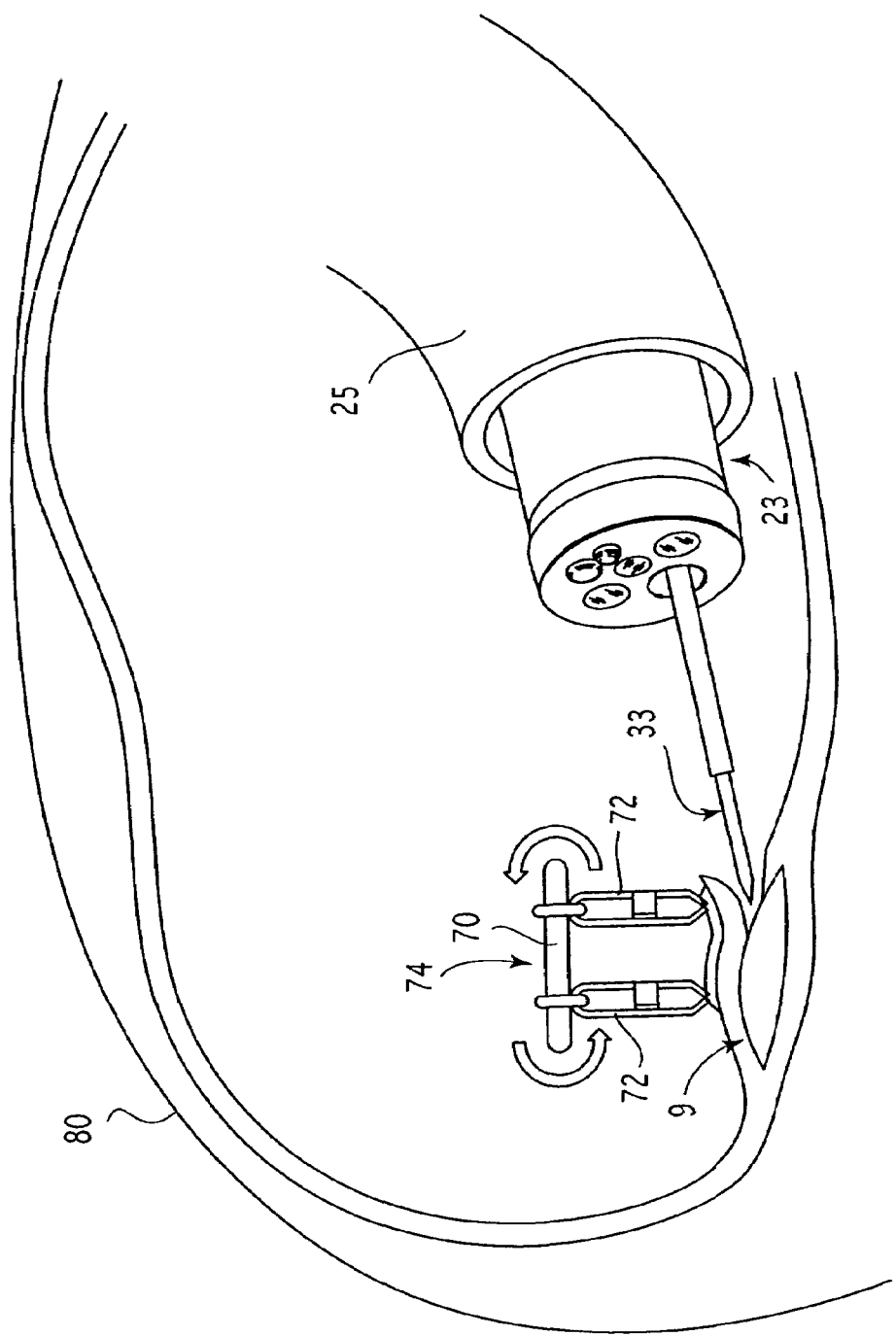
FIG. 20 is a view of a magnetic anchor guide apparatus using a rotating engagement member according to a modification of the fourth embodiment of the present invention.
Figure 21:
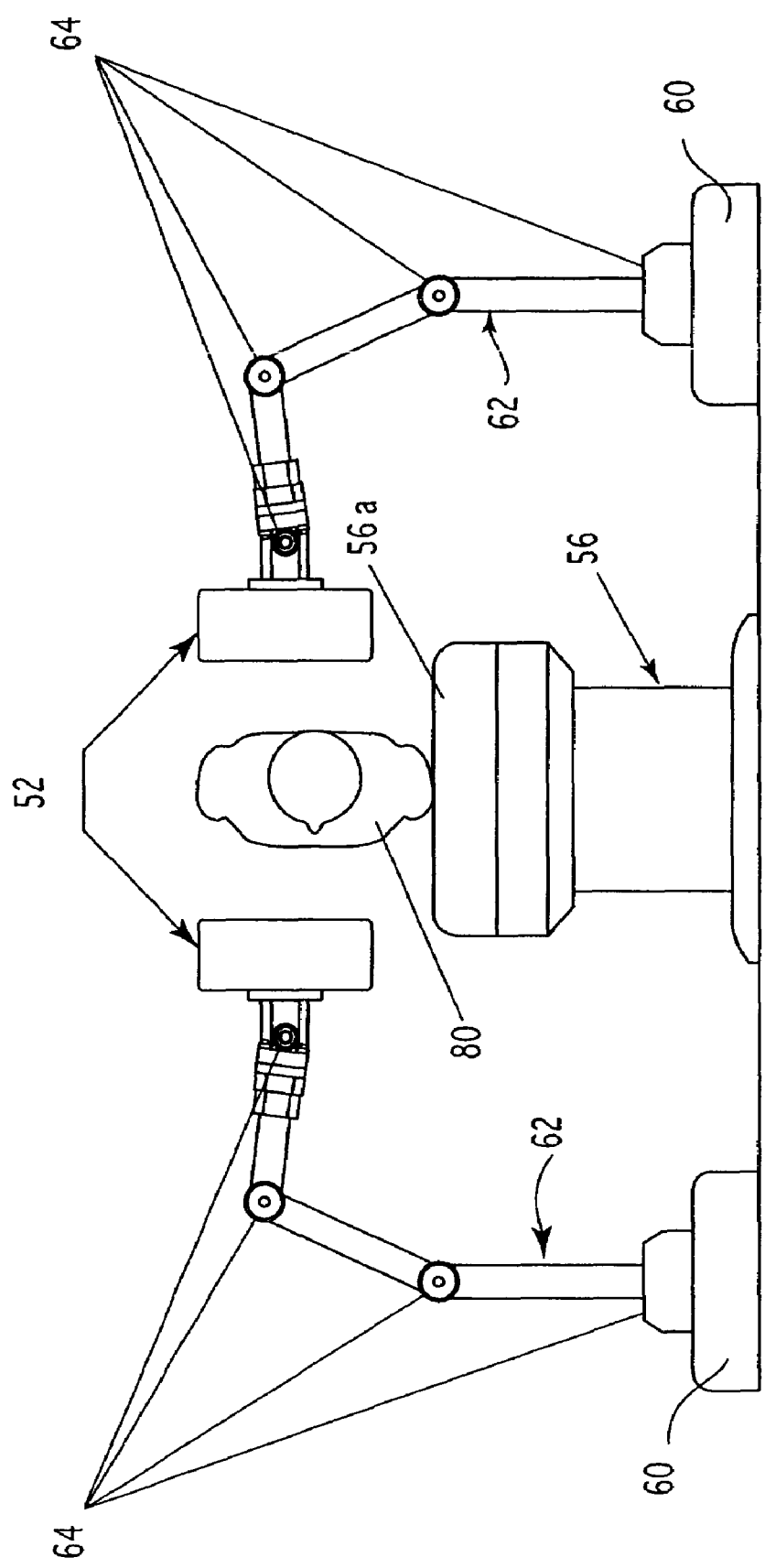
FIG. 21 is a view of a magnetic anchor guide apparatus according to a modification of the fourth embodiment of the present invention.

Several modified embodiments will be discussed below. As shown in FIG. 19, an engagement member 74 constructed from a bar member 70 and clips 72 hung from the bar member 70 at the opposed ends thereof can be used instead of the clip 3 and the fishhook-shaped engagement member 45. The bar member 70 is magnetized north at one end thereof and magnetized south at the other end. Consequently, the magnetized north end and the magnetized south end of the bar member 70 are oriented in the N-pole direction and S-pole direction of the resultant magnetic field produced by the four magnetic guide members 52. Therefore, the direction of the bar member 70 is changed in accordance with the resultant magnetic field which is varied by controlling the electric current supplied to the four magnetic guide members 52. With this arrangement, the engagement member 74 can be powered by the resultant magnetic field applied to the clips 72 provided at the opposite ends of the bar member 70 to optionally vary the direction and the height of the engagement member 74. The number of the magnetic guide members 52 is at least two. Alternatively, it is also possible to provide two assemblies of the arms 62 and the magnetic guide members 52 supported thereon, as in the third embodiment, on the front and rear sides of the patient 80, as shown in FIG. 21. The remaining structure, other operations and effects of the invention are the same as those in the first embodiment.

Further modifications of the invention will be discussed below.

Figure 22B:
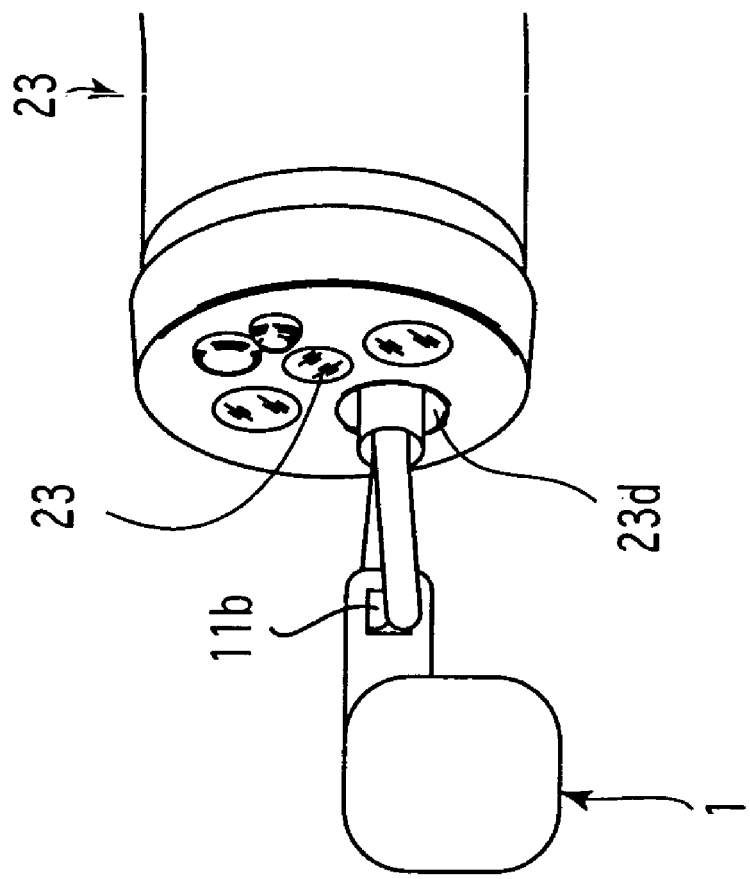
FIG. 22B is a perspective view of the embodiment shown in FIG. 22A.
Figure 22A:
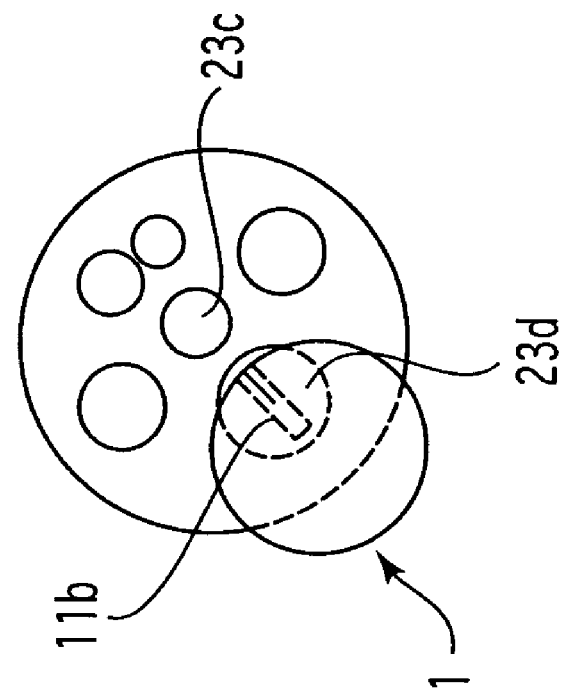
FIG. 22A is a front elevational view of a modified embodiment of the present invention in which a hole arrangement of a magnetic anchor is modified.

The magnetic anchor 1 can be provided with a hole 11b at the end portion thereof, as shown in FIGS. 22A and 22B.

Figure 23B:
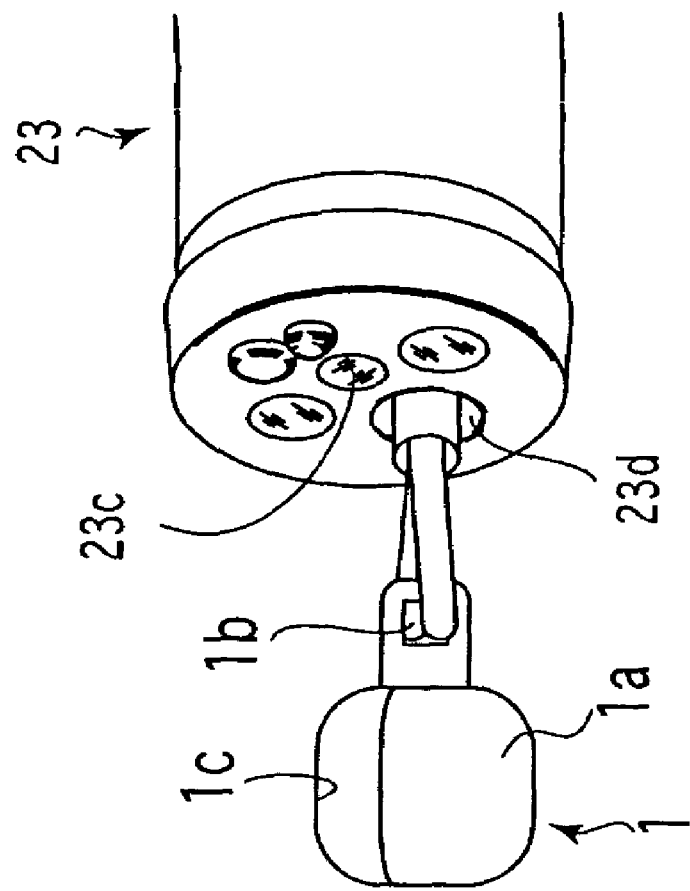
FIG. 23B is a perspective view of the embodiment shown in FIG. 23A.
Figure 23A:
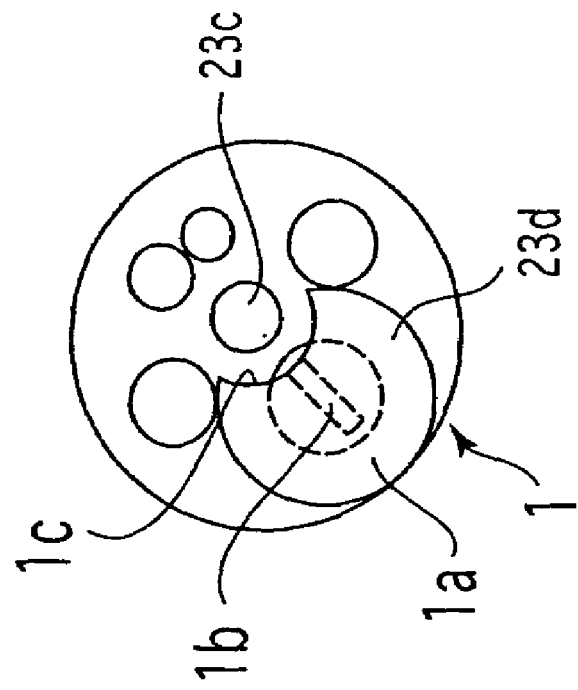
FIG. 23A is a front elevational view of a modified embodiment of a magnetic anchor in which a cut-away portion is provided in the magnetic anchor.
Figure 24:
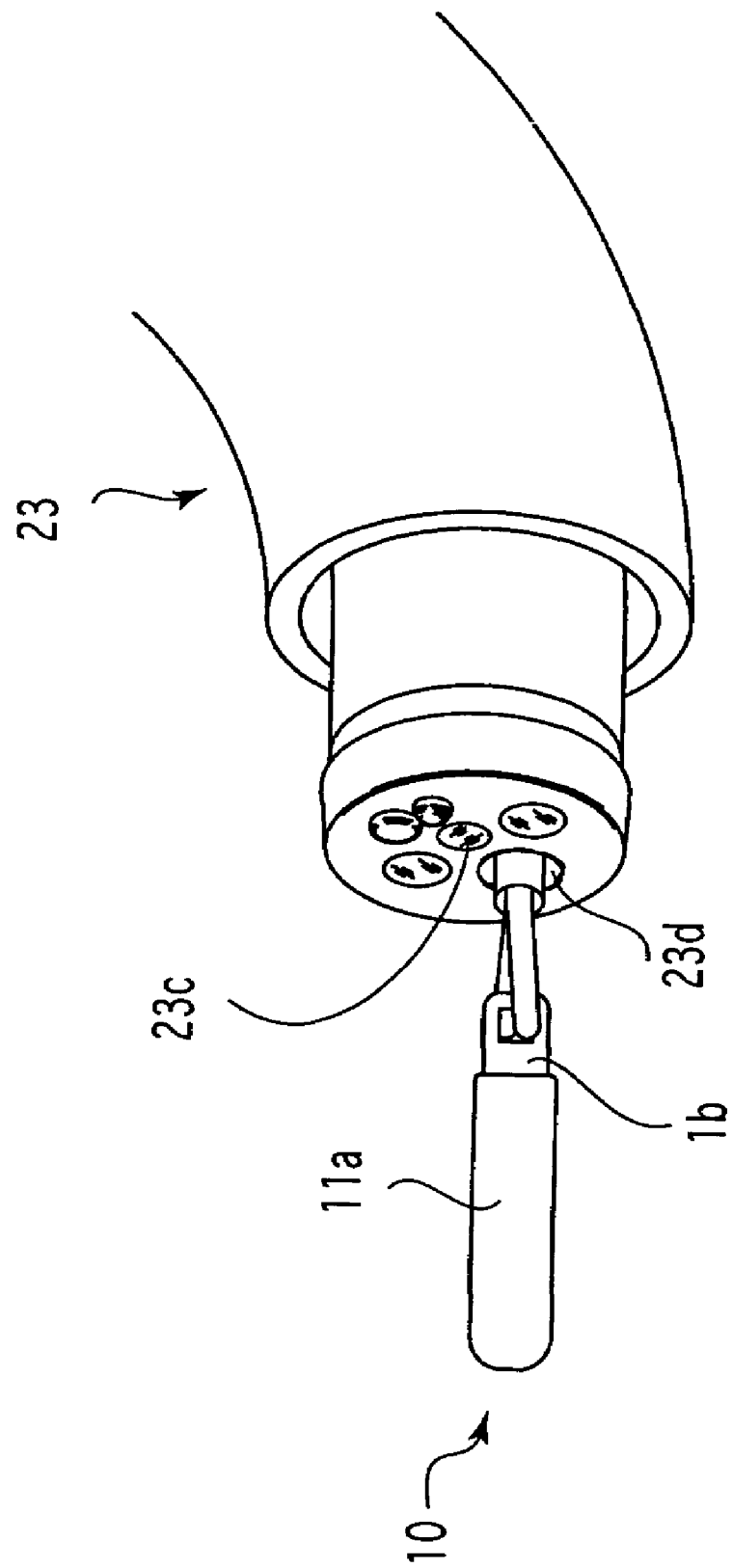
FIG. 24 is a view of a modified embodiment of a magnetic anchor having a different shape.

Alternatively, as shown in FIGS. 23A and 23B, the main body 1a of the magnetic anchor 1 can be partly cut away, as indicated at 1c. Moreover, as shown in FIG. 24, the main body 11a of a magnetic anchor 10 can be in the form of a bar whose diameter is substantially identical to the diameter of the forceps channel 23d.

Figure 25:
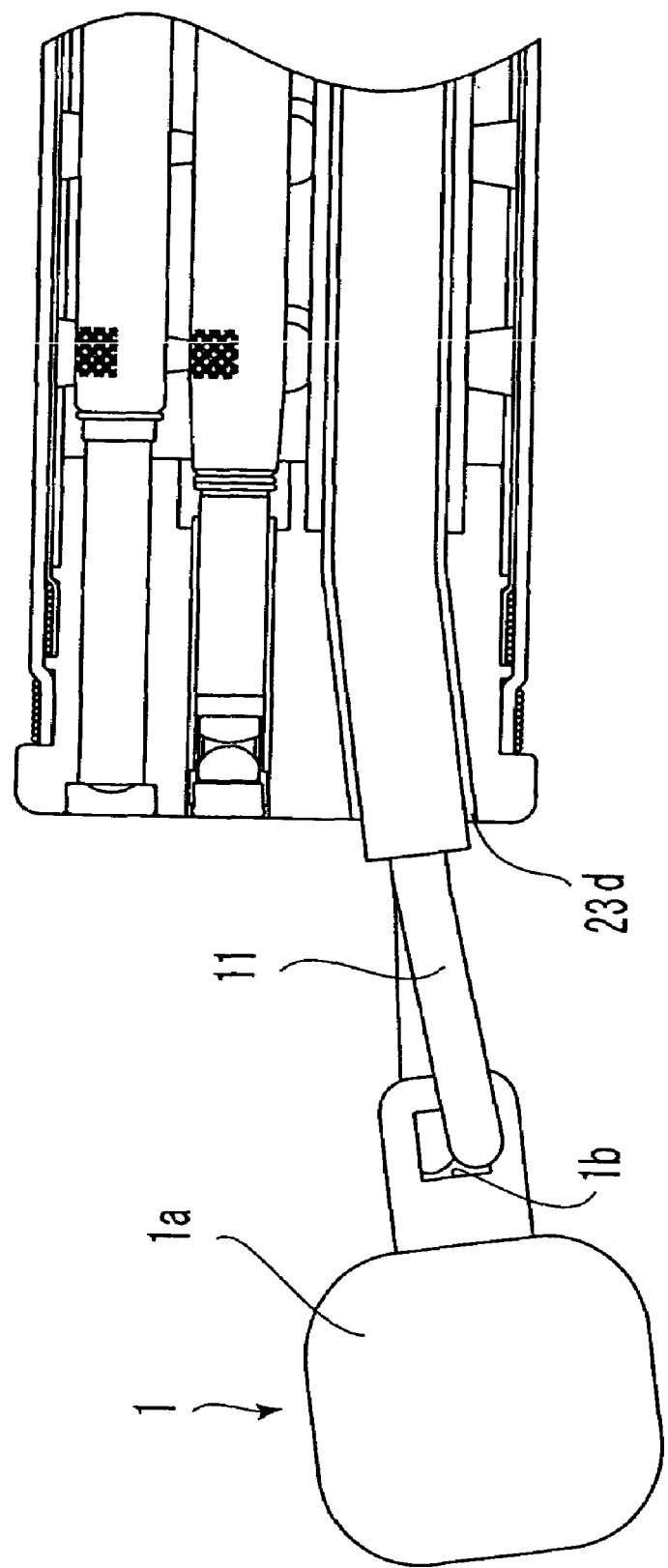
FIG. 25 is a view of a modified embodiment of the present invention in which the shape of a forceps channel is modified.

Alternatively, as shown in FIG. 25, the front end of the forceps channel 23d can be bent downwardly. With this structure, as the field of view through the view window 23c is not restricted by the magnetic anchor 1, the resection of the diseased portion can be carried out more precisely and speedily.

Figure 26:
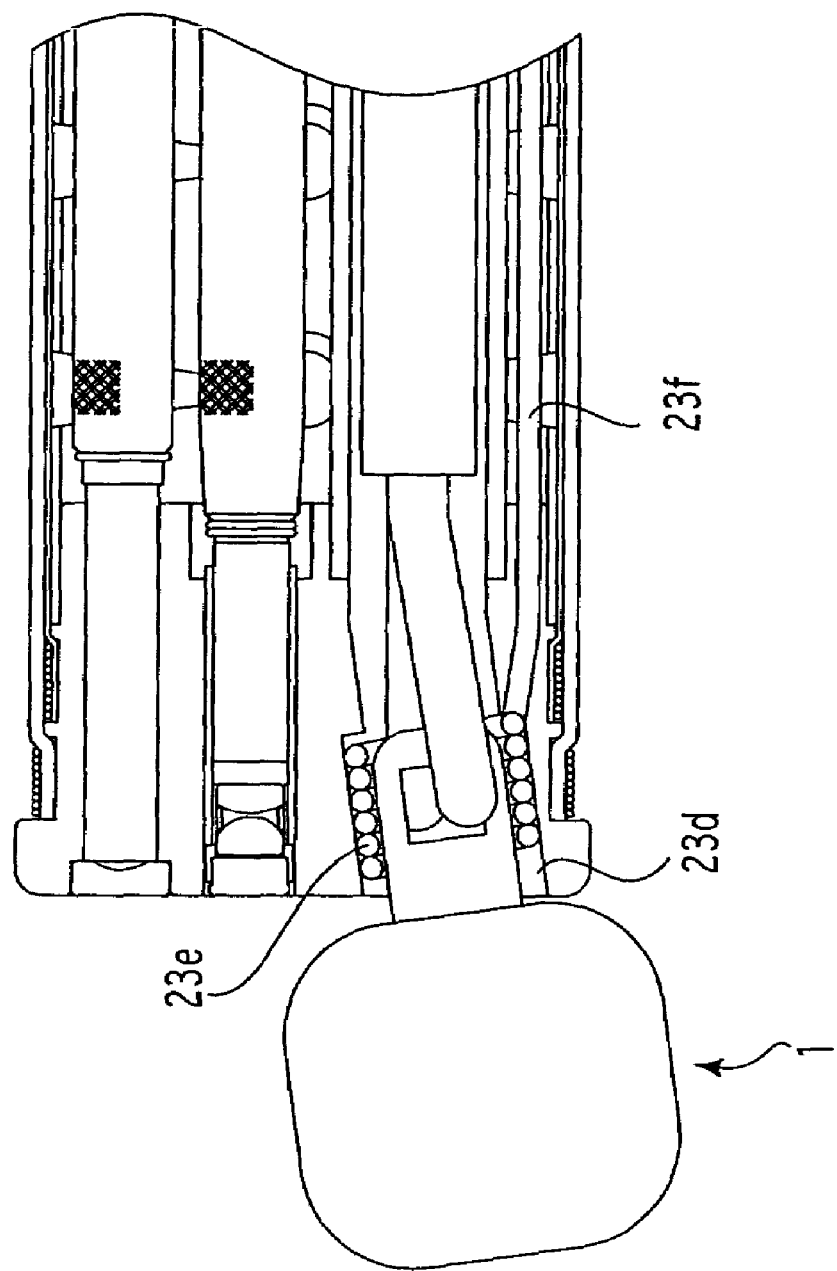
FIG. 26 is a view of a modified embodiment of the present invention in which a coil is arranged in a forceps channel.

As shown in FIG. 26, it is possible to provide a coil 23e at the front end of the forceps channel 23d, so that the electric current is supplied to the coil 23e through a conductor 23f to form an electromagnet.

Figure 27:
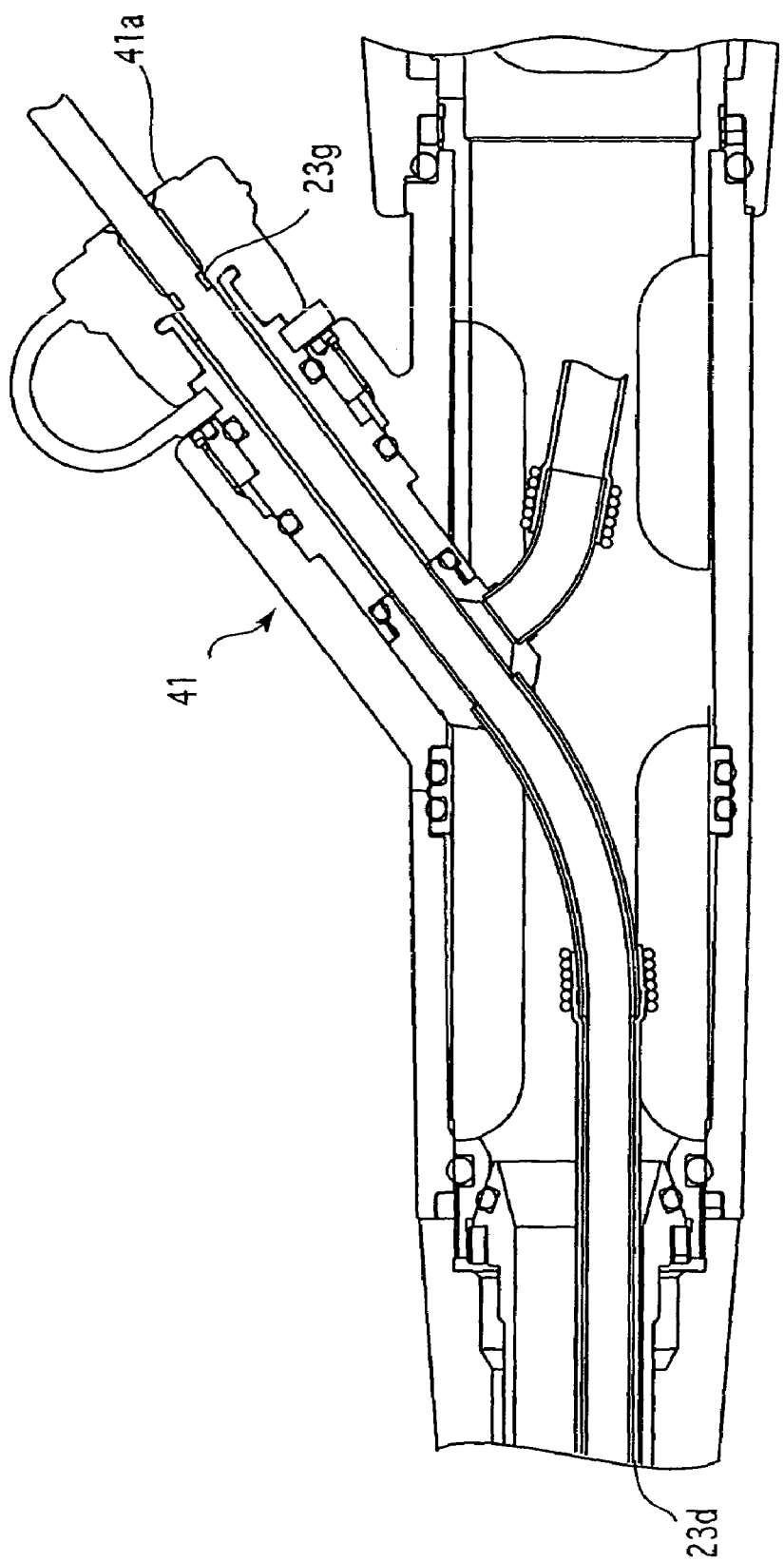
FIG. 27 is a view of a modified embodiment of the present invention in which a forceps channel is provided therein with a restricting portion.

Alternatively, as shown in FIG. 27, it is possible to provide a restricting portion 23g in the forceps channel 23d adjacent to the forceps insertion opening 41a of the endoscope 41. With this structure, it is possible to prevent the clamping forceps 11, which hold at the front end thereof the magnetic anchor 1, from accidentally falling in the patient's body 80 due to the dead weight of the magnetic anchor 1.

Although the above discussion has been addressed to the embodiments, the present invention is not limited to the embodiments discussed above. Various modifications can be made without departing from the object and spirit of the invention.

As can be understood from the foregoing, according to the present invention, as the diseased portion can be sufficiently raised, a sufficient amount of the portion to be cut at the boundary between the diseased portion and the normal tissue can be provided. Moreover, if the diseased portion is flat, the portion to be cut can be produced. If the diseased portion is large, there is no chance of the cut diseased portion falling onto the normal tissue during the resection operation. Consequently, the field of view of the endoscope is less obstructed. As a result, there is no chance of resection being carried out blindly, the normal portion being injured leading to complications such as perforation, the blood vessel being damaged leading to heavy bleeding, nor hemostasis not being able to be carried out due to the bleeding portion not being visually confirmed, leading to serious complications.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A magnetic anchor remote guidance system comprising:
   an engagement member configured to engage with a body portion in a patient's body;
   a magnetic anchor comprising a magnetic material, and connectable to the engagement member; and
   a magnetic anchor guide device positioned externally of the patient's body and configured to produce a magnetic field to power the magnetic anchor;
   wherein the body portion engaged by the engagement member is raised by supplying power to the magnetic anchor via the magnetic field produced by the magnetic anchor guide device;
   wherein the engagement member comprises a clip.

2. The magnetic anchor remote guidance system according to claim 1, wherein the magnetic anchor and the engagement member are interconnected in advance.

3. The magnetic anchor remote guidance system according to claim 1, wherein the magnetic anchor guide device comprises:
   a magnetic guide member which produces the magnetic field to power the magnetic anchor;
   a two-dimensional moving mechanism which moves the magnetic guide member along a U-shaped frame which is arranged in a specific plane; and
   a unidirectional moving mechanism which relatively moves the U-shaped frame in a direction perpendicular to the specific plane.

4. The magnetic anchor remote guidance system according to claim 1, wherein the magnetic anchor guide device comprises:
   a magnetic guide member which produces the magnetic field to power the magnetic anchor; and an arm member which is supported on a main body which is movable on a support surface, the arm being bendable at an articulated joint, so that the magnetic guide member is movable by adjusting a bending angle of the arm at the articulated joint.

5. The magnetic anchor remote guidance system according to claim 1, wherein the magnetic anchor guide device comprises a plurality of magnetic guide devices in which the magnetic fields produced thereby are independently adjustable, so that the magnetic anchor can be powered by the resultant magnetic field of the magnetic guide devices.

6. The magnetic anchor remote guidance system according to claim 1, said engagement member being configured to engage and raise the body portion and the magnetic anchor being configured to position the engagement member with respect to the body portion.

7. The magnetic anchor remote guidance system according to claim 1, said engagement member being configured for insertion into a patient's body via an insertion mechanism, said engagement member engaging the body portion when the engagement member is separate from the insertion mechanism.

8. The magnetic anchor remote guidance system according to claim 1, wherein said magnetic anchor and said engagement member are each connected to a connector, said engagement member, said connector and at least a part of said magnetic anchor being inserted into the patient's body while positioned within a guide sheath.

9. The magnetic anchor remote guidance system according to claim 8, said connector configured to be expelled from said guide sheath.

10. The magnetic anchor remote guidance system according to claim 8, said guide sheath being severable.

11. The magnetic anchor remote guidance system according to claim 1, wherein said engagement member is configured for insertion into the patient's body via a channel of an endoscope.

12. A magnetic anchor apparatus comprising:
an engagement member which is configured to engage with and to raise a body portion in a patient's body; and
a magnetic anchor comprising a magnetic material, said magnetic anchor connectable to said engagement member and configured to move said engagement member to raise the body portion engaged by said engagement member;
wherein the magnetic anchor is configured to move the engagement member to raise the body portion when power is supplied to a magnetic anchor guide device positioned externally of the patient's body to generate a magnetic field; and
wherein the engagement member comprises a clip.

13. A magnetic anchor remote guidance system comprising:
an engagement member having a fish hook shape and configured to engage with a body portion in a patient's body;
a magnetic anchor comprising a magnetic material, and connectable to the engagement member; and
a magnetic anchor guide device positioned externally of the patient's body and configured to produce a magnetic field to power the magnetic anchor;
wherein the body portion engaged by the engagement member is raised by supplying power to the magnetic anchor via the magnetic field produced by the magnetic anchor guide device.

14. A magnetic anchor remote guidance system comprising:
an engagement member configured to engage with a body portion in a patient's body;
a magnetic anchor comprising a magnetic material, and connectable to the engagement member;
a magnetic anchor guide device positioned externally of the patient's body and configured to produce a magnetic field to power the magnetic anchor;
wherein the body portion engaged by the engagement member is raised by supplying power to the magnetic anchor via the magnetic field produced by the magnetic anchor guide device; and
a connector for connecting the magnetic anchor with the engagement member, the connector being extendible and contractible.

15. A magnetic anchor remote guidance system comprising:
an engagement member configured to engage with a body portion in a patient's body;
a magnetic anchor comprising a magnetic material, and connectable to the engagement member; and
a magnetic anchor guide device positioned externally of the patient's body and configured to produce a magnetic field to power the magnetic anchor;
wherein the body portion engaged by the engagement member is raised by supplying power to the magnetic anchor via the magnetic field produced by the magnetic anchor guide device;
said engagement member comprising a carrying member including at least two body portion raising members, said carrying member comprising a magnetized member, said at least two body portion raising members being attached to said magnetized member.

16. A magnetic anchor apparatus comprising:
an engagement member having a fish hook shape and being configured to engage with and to raise a body portion in a patient's body; and
a magnetic anchor comprising a magnetic material, said magnetic anchor connectable to said engagement member and configured to move said engagement member to raise the body portion engaged by said engagement member;
wherein the magnetic anchor is configured to move the engagement member to raise the body portion when power is supplied to a magnetic anchor guide device positioned externally of the patient's body to generate a magnetic field.

17. A magnetic anchor apparatus comprising:
an engagement member which is configured to engage with and to raise a body portion in a patient's body;
a magnetic anchor comprising a magnetic material, said magnetic anchor connectable to said engagement member and configured to move said engagement member to raise the body portion engaged by said engagement member;
wherein the magnetic anchor is configured to move the engagement member to raise the body portion when power is supplied to a magnetic anchor guide device positioned externally of the patient's body to generate a magnetic field, the magnetic anchor remote guidance system comprising a connector for connecting the magnetic anchor with the engagement member, the connector being extendible and contractible.

18. A magnetic anchor apparatus comprising:
an engagement member which is configured to engage with and to raise a body portion in a patient's body; and
a magnetic anchor comprising a magnetic material, said magnetic anchor connectable to said engagement member and configured to move said engagement member to raise the body portion engaged by said engagement member;

wherein the magnetic anchor is configured to move the engagement member to raise the body portion when power is supplied to a magnetic anchor guide device positioned externally of the patient's body to generate a magnetic field;

said engagement member comprising a carrying member including at least two body portion raising members, said carrying member comprising a magnetized member, said at least two body portion raising members being attached to said magnetized member.

* * * * *